United States Patent
Zwiefelhofer et al.

(10) Patent No.: US 12,071,654 B2
(45) Date of Patent: Aug. 27, 2024

(54) CAPTURE PROBE-BASED LIBRARY NORMALIZATION

(71) Applicant: Sequenom, Inc., San Diego, CA (US)

(72) Inventors: Tricia Zwiefelhofer, San Diego, CA (US); Jason Nathanson, San Diego, CA (US)

(73) Assignee: SEQUENOM, INC, San Diego, CA (US)

( * ) Notice: Subject to any disclaimer, the term of this patent is extended or adjusted under 35 U.S.C. 154(b) by 383 days.

(21) Appl. No.: 16/837,425

(22) Filed: Apr. 1, 2020

(65) Prior Publication Data
US 2020/0308637 A1    Oct. 1, 2020

Related U.S. Application Data

(60) Provisional application No. 62/827,601, filed on Apr. 1, 2019.

(51) Int. Cl.
*C12Q 1/6837*    (2018.01)
*C12Q 1/6874*    (2018.01)
*C40B 40/06*    (2006.01)

(52) U.S. Cl.
CPC ......... *C12Q 1/6837* (2013.01); *C12Q 1/6874* (2013.01); *C40B 40/06* (2013.01); *C12Q 2600/158* (2013.01)

(58) Field of Classification Search
CPC .................................................. C12Q 1/6837
See application file for complete search history.

(56) References Cited

U.S. PATENT DOCUMENTS

| | | |
|---|---|---|
| 7,439,014 B1 | 10/2008 | Pamula et al. |
| 10,961,562 B2 * | 3/2021 | Makarov ................ C12Q 1/686 |
| 2016/0046987 A1 * | 2/2016 | Kim ................... C12N 15/1013 |
| | | 506/26 |

OTHER PUBLICATIONS

Chen et al., "Whole-Exome Enrichment with the Illumina TruSeq Exome Enrichment Platform," Cold Spring Harb Protoc 2015, 7: 642-648. (Year: 2015).*
Clark et al., "Performance comparison of exome DNA sequencing technologies," Nat. Biotechnol. 2011, 29(10): 908-914, with 2 pages of "Online Methods". (Year: 2011).*
Okayama, H., and Berg, P., "High-Efficiency Cloning of Full-Length cDNA," Mol. Cell Biol. 2:161-170 (1982).

* cited by examiner

*Primary Examiner* — Kaijiang Zhang
(74) *Attorney, Agent, or Firm* — Kilpatrick Townsend & Stockton LLP

(57) ABSTRACT

Provided herein are methods of normalizing nucleic acid libraries. The method uses nucleic acid probes with nucleic acid sequences that are complementary to one or more of these adaptor sequences are added to the nucleic acids libraries. The probes can hybridize to the adaptor sequences in the single stranded nucleic acid molecules derived from the libraries to form hybridization complexes. The probes are conjugated to a first binding member, which can interact with a second binding member that is conjugated to solid supports. The solid supports can then be collected and the single stranded nucleic acid molecules can be recovered in a volume of elution buffer to reach a desired concentration. As compared to standard methods, the methods are more efficient and cost-effective.

29 Claims, 14 Drawing Sheets

Specification includes a Sequence Listing.

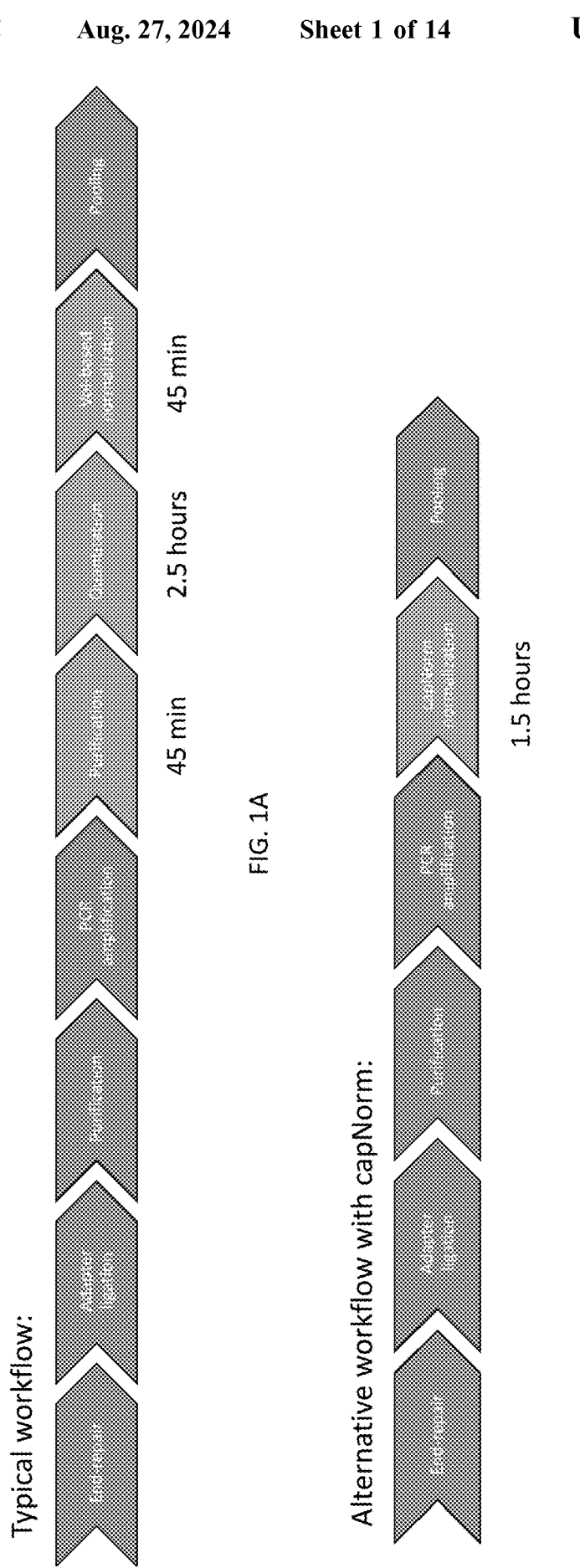

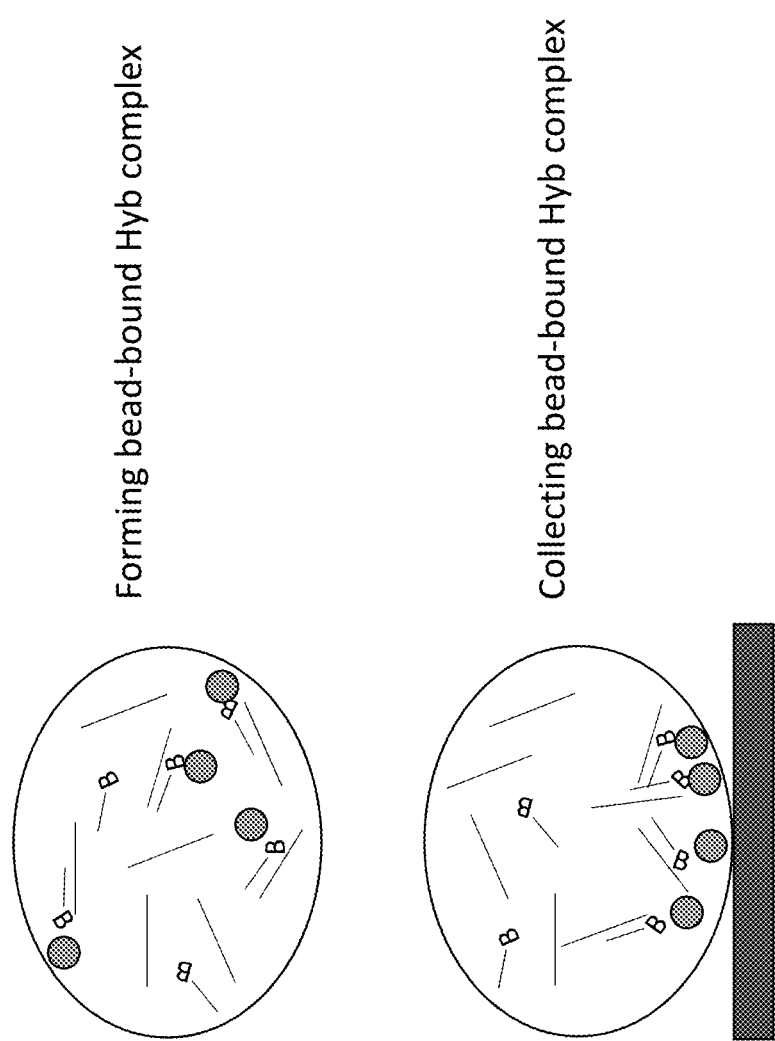

Exemplary library construct after adapter ligation and PCR amplification (I)

Library sequence:
5' - AATGATACGGCGACCACCGAGATCTACAC[i5]ACACTCTTTCCCTACACGACGCTCTTCCGATCT – DNA Insert - AGATCGGAAGAGCACACGTCTGAACTCCAGTCAC[i7]ATCTCGTATGCCGTCTTCTGCTTG - 3'
(SEQ ID NO: 18) (SEQ ID NO: 19) (SEQ ID NO: 14) (SEQ ID NO: 15)

Reverse complement of library sequence:
5' - CAAGCAGAAGACGGCATACGAGAT[i7]GTGACTGGAGTTCAGACGTGTGCTCTTCCGATCT – DNA Insert - AGATCGGAAGAGCGTCGTGTAGGGAAAGAGTGT[i5]GTGTAGATCGGTGTGGTCGCCGTATCATT - 3'
(SEQ ID NO: 12) (SEQ ID NO: 17) (SEQ ID NO: 20) (SEQ ID NO: 21)

Double-stranded library with strands in relative (hybridized) orientation:

5' - AATGATACGGCGACCACCGAGATCTACAC[i5]ACACTCTTTCCCTACACGACGCTCTTCCGATCT – DNA Insert - AGATCGGAAGAGCACACGTCTGAACTCCAGTCAC[i7]ATCTCGTATGCCGTCTTCTGCTTG - 3'
(SEQ ID NO: 18) (SEQ ID NO: 19) (SEQ ID NO: 14) (SEQ ID NO: 15)

3' - TTACTATGCCGCTGGTGGCTCTAGATGTG[i5]TGTGAGAAAGGGATGTGCTGCGAGAAGGCTAGA – DNA Insert - TCTAGCCTTCTCGTGTGCAGACTTGAGGTCAGTG[i7]TAGAGCATACGGCAGAAGACGAAC - 5'
(SEQ ID NO: 21) (SEQ ID NO: 20) (SEQ ID NO: 17) (SEQ ID NO: 12)

P5 adaptor ⎱ ⎰ P7 adaptor

FIG. 7

Exemplary capNorm Capture Probes capNorm capture probe (BioTinTEG-ILMN_P5f):
5' - BioTinTEG - CCTACACGACGCTCTTCCGATCT - 3'   (SEQ ID NO: 3)

capNorm capture probe (BioTinTEG-ILMN_P5rc):
5' - BioTinTEG - GTGTAGGGAAAGAGTGTAGATCTCGGT - 3'   (SEQ ID NO: 4)

Double-stranded library with strands in relative orientation, denatured, with capNorm probes aligned to hybridization sequence:

5' - AATGATACGGCGACCACCGAGATCTACACTCTTTCCCTACACGACGCTCTTCCGATCT - AGATCGGAAGAGCACACGTCTGAACTCCAGTCAC[i7]ATCTCGTATGCCGTCTTCTGCTTG - 3' (SEQ ID NO: 1)

5' - BioTinTEG - GTGTAGGGAAAGAGTGTAGATCTCGGT - 3' (SEQ ID NO: 4)

5' - BioTinTEG - CCTACACGACGCTCTTCCGATCT - 3' (SEQ ID NO: 3) — DNA Insert - AGATCGGAAGAGCACACGTCTGAACTCCAGTCAC[i7]ATCTCGTATGCCGTCTTCTGCTTG - 3' (SEQ ID NO: 15)

5' - CAAGCAGAAGACGGCATACGAGAT[i7]GTGACTGGAGTTCAGACGTGTGCTCTTCCGATCT — DNA Insert - AGATCGGAAGAGCGTCGTGTAGGGAAAGAGTGTAGATCTCGGTGGTCGCCGTATCATT - 3' (SEQ ID NO: 16)

5' - CAAGCAGAAGACGGCATACGAGAT[i7]GTGACTGGAGTTCAGACGTGTGCTCTTCCGATCT (SEQ ID NO: 17)

FIG. 9

CAPTURE PROBE-BASED LIBRARY NORMALIZATION

CROSS REFERENCE TO RELATED APPLICATION

This application claims priority to U.S. Provisional Application No. 62/827,601, filed on Apr. 1, 2019, the entire content of which is herein incorporated by reference for all purposes.

SEQUENCE LISTING

The instant application contains a Sequence Listing which has been submitted electronically in ASCII format and is hereby incorporated by reference in its entirety. Said ASCII copy, created on Mar. 30, 2020, is named 057618-1174459_SL.txt and is 4,892 bytes in size.

FIELD

This disclosure relates to normalization of nucleic acid libraries.

BACKGROUND

High throughput assays have been widely used to assess biochemical and molecular profiles of sample nucleic acid libraries. The libraries are often pooled for efficiency and the concentrations of these individual libraries may vary widely. The disparity can adversely affect the downstream assay's specificity and sensitivity. For example, libraries that are of low concentrations are underrepresented in the assay results, and are thus less likely to be detected for the feature of interest; this could lead to false negative results. Conversely, libraries that are of high concentrations dominate the assay results with little contribution to the interpretation of experimental results; this would increase the cost of the high throughput assay. In the context of next generation sequencing, if libraries (one library typically represent one patient sample) are not normalized prior to pooling and sequencing, then the range of aligned reads per patient sample will be very broad. Some patient samples will yield far more reads than is necessary for the test while others will not generate enough reads and will fail QC metrics. Thus, these nucleic acid libraries need to be normalized before being used for these assays.

Conventional methods for normalizing nucleic acid libraries are labor intensive and inefficient. Typically, after nucleic acid molecules are ligated with adaptors and amplified, the resultant libraries are purified and their concentrations are measured. Based on the concentrations, each of the libraries is diluted individually to a volume that is determined based on the desired concentration and the measured concentration. These methods are often referred to as the volume-based normalization methods. A typical workflow of a volume-based normalization method is shown in FIG. 1A, which typically takes about 4-5 hours. These methods are referred to as the standard methods in this disclosure.

A need exists for a faster and more efficient method to normalize nucleic acid libraries and for normalized nucleic acid libraries produced by such method.

SUMMARY OF THE INVENTION

In some embodiments, this disclosure provides a method for normalizing a nucleic acid library comprising: (a) hybridizing single stranded nucleic acid molecules obtained from the library with probes to form hybridization complexes, wherein the single stranded nucleic acid molecules each comprise an A adaptor sequence and a B adaptor sequence, or an A' adaptor sequence and a B' adaptor sequence, wherein each hybridization complex comprises one of the single-stranded nucleic acid molecules and one or more probes, wherein the one or more probes each has a sequence that is complementary to the A adaptor sequence, the B adaptor sequence, the A' adaptor sequence, or the B' adaptor sequence, and wherein the one or more probes each is conjugated to a first binding member, (b) contacting the hybridization complexes with solid supports, each solid support conjugated to a second binding member, wherein the first binding member binds to the second binding member, thereby causing the solid supports to bind to the hybridization complexes to form solid support-bound hybridization complexes, (c) collecting the solid support-bound hybridization complexes, and (d) separating the single stranded nucleic acid molecules from probes in the hybridization complexes, thereby obtaining a normalized library of single stranded nucleic acid molecules. The A adaptor sequence is a reverse complement of the A' adaptor sequence, and the B adaptor sequence is a reverse complement of the B' adaptor sequence.

In some embodiments, step (a) comprises mixing the probes with the single stranded nucleic acid molecules to form a hybridization mixture, wherein the amount of the probe as compared to single stranded nucleic acid molecules is selected to normalize libraries, such that the range of relative variation in concentration of normalized libraries as compared to the range of relative variation in concentration of pre-normalized libraries is reduced by at least 30%.

In some embodiments, the A adaptor is a P5 adaptor and the B adaptor is a P7 adaptor, wherein the P5 adaptor and the P7 adaptor are configured for analyzing the libraries in next generation sequencing. The A adaptor and the B adaptor are double-stranded adaptors. The A adaptor comprises an A adaptor sequence and an A' adaptor sequence. The B adaptor comprises a B adaptor sequence and a B' adaptor sequence, which are reverse complementary to each other.

In some embodiments, the method further comprises washing the collected solid support-bound hybridization complexes after step (c) and before step (d).

In some embodiments, the nucleic acid molecules in the nucleic acid library are double stranded, wherein the method further comprises denaturing the double stranded nucleic acid molecules to produce the single stranded nucleic acid molecules.

In some embodiments, the first binding member is biotin and the second binding member is selected from streptavidin, avidin and neutrAvidin.

In some embodiments, the first binding member binds to the second binding member through antibody antigen interaction.

In some embodiments, the single stranded nucleic acid molecules comprise a first single stranded nucleic acid and a second single stranded nucleic acid, wherein the first single stranded nucleic acid is complementary to the second single stranded nucleic acid, and wherein the first single stranded nucleic acid comprises an A adaptor sequence and a B adaptor sequence, and the second single stranded nucleic acid comprises an A' adaptor sequence and B' adaptor sequence.

In some embodiments, the step (a) comprises: hybridizing one or more first probes to the first strand to form a first hybridization complex, wherein the one or more first probes are complementary to the A adaptor sequence or the B adaptor sequence, and/or hybridizing one or more second probes to the second strand to form a second hybridization complex, wherein the one or more second probes are complementary to the A' adaptor sequence or the B' adaptor sequence.

In some embodiments, each of the one or more first probes shares no more than 10 consecutive complementary nucleotides with each of the one or more second probes. In some embodiments, each of the one or more first probes shares no more than 7 consecutive complementary nucleotides with each of the one or more second probes. In some embodiments, each of the one or more first probes shares no complementary nucleotide with the one or more second probes.

In some embodiments, the one or more probes each has a length of 18 to 35 nucleotides. In some embodiments, the one or more probes has a sequence of SEQ ID NO: 3 or SEQ ID NO: 4.

In some embodiments, the solid supports are beads. In some embodiments, the beads are paramagnetic beads and the collecting the complexes is by placing the complexes in a magnetic field.

In some embodiments, the one or more probes each further comprise a spacer between the first binding member and its nucleic acid sequence, wherein the spacer comprises a simple carbon or ethylene glycol chain, or multiples of either.

In some embodiments, hybridizing single stranded nucleic acid molecules with probes is by mixing the probes with the single stranded nucleic acid molecules to form a hybridization mixture, wherein the ratio of the molar amount of the probes to the molar amount of single stranded nucleic acids ranges from 0.025:1 to 16.7:1.

In some embodiments, the concentration of the double stranded nucleic acid library ranges from 15 nM to 200 nM. In some embodiments, the total concentration of the probes ranges from 10 nM to 500 nM. In some embodiments, the amount of the solid supports ranges from 50 to 600 μg per reaction. In some embodiments, the denaturing is under the temperature that ranges from 102° C. -110° C. In some embodiments, the single stranded nucleic acid molecules are hybridized to probes for a period of time that ranges from 8 to 16 minutes. In some embodiments, step (b) comprising incubating the hybridization complexes with the solid supports for a period of time that ranges from 20 to 40 minutes.

In some embodiments, the A adaptor sequence, the A' adaptor sequence, the B adaptor sequence, or the B' adaptor sequence are configured to be able to bind to an oligo immobilized on a flow cell of a sequencer. In some embodiments, one or more of the A adaptor sequence, the A' adaptor sequence, the B adaptor sequence, or the B' adaptor sequence comprises a sample index sequence. In some embodiments, the A adaptor sequence comprises SEQ ID NO: 10 and the B adaptor sequence comprise SEQ ID NO: 13. In some embodiments, the A' adaptor sequence comprises SEQ ID NO: 11, and the B' adaptor sequence comprises SEQ ID NO: 12. In some embodiments, the method further comprises sequencing the normalized library of single stranded nucleic acid molecules.

This disclosure also provides a hybridization solution comprising one or more probes and a salt, wherein one or more probes each have a sequence that is complementary to the A adaptor sequence, the B adaptor sequence, the A' adaptor sequence, or the B' adaptor sequence, wherein the one or more probes, each conjugated to a first binding member. In some embodiments, the salt is present in a concentration ranging from 75 mM to 1200 mM. In some embodiments, the first binding member is biotin. In some embodiments, the one or more probes have the same sequence. In some embodiments, the one or more probes comprises a first probe and a second probe, wherein the first probe being complementary to the A adaptor sequence or the B adaptor sequence, and the second probe being complementary to the A' adaptor sequence or the B' adaptor sequence.

Also provided in this disclosure is a reaction mixture comprising a hybridization solution of any of embodiments 30-34 and single stranded nucleic acid molecules. In some embodiments, the reaction mixture further comprises a solid support. In some embodiments, the solid support is a paramagnetic bead.

Also provided herein is a kit comprising (i) probes each have a sequence that is complementary to the A adaptor sequence, the B adaptor sequence, the A' adaptor sequence, or the B' adaptor sequence, and (ii) a paramagnetic solid support, wherein the solid support is conjugated to a second binding member, and wherein the first binding member is capable of binding to the second binding member. In some embodiments, the probes comprise one or more first probes have a sequence that is complementary to the A adaptor sequence or the B adaptor sequence, and one or more second probes have a sequence that is complementary to the A' adaptor sequence and the B' adaptor sequence. In some embodiments, the one or more first probes have a sequence of SEQ ID NO: 3 and the one or more second probes have a sequence of SEQ ID NO: 4.

Also provided herein is a method of normalizing a plurality of nucleic acid libraries which are of different concentrations in a pre-normalized range, wherein the method comprises: normalizing each library according to any of the embodiments above to obtain a normalized library, whereby producing a plurality of normalized libraries of different concentrations in a normalized range, wherein the normalized range is narrower than the pre-normalized range. In some embodiments, the relative variation in concentration among the normalized libraries is not greater than 8 fold. In some embodiments, the method further comprises sequencing the single-stranded nucleic acid molecules from each normalized library, and determining total aligned sequencing counts, wherein the standard deviation for the total aligned sequencing counts is within 25% of the mean aligned sequencing counts.

In some embodiments, normalizing each library according to any of the embodiments disclosed above comprises hybridizing single stranded nucleic acid molecules with probes is by mixing the probes with the single stranded nucleic acid molecules to form a hybridization mixture, wherein the ratio of the molar amount of the probes to the molar amount of single stranded nucleic acids in the hybridization mixture ranges from 0.025:1 to 16.7:1.

BRIEF DESCRIPTION OF THE DRAWINGS

FIGS. 1A and 1B illustrate the workflow of library preparation for high throughput assays. The flow chart on the top (FIG. 1A) is the standard method and the flow chart on the bottom (FIG. 1B) is the method disclosed herein: the capNorm method.

FIG. 2A-2C illustrates the methods steps used in capNorm.

In FIG. 3A-3I, P5, P5', P7, and P7' represent the P5 adaptor sequence, the P5' adaptor sequence, the P7 adaptor sequence, and the P7' adaptor sequence.

FIGS. 4A and 4B are different representations of the same data, showing that the non-normalized libraries were significantly more variable in terms of the total aligned sequencing counts than normalized libraries. The Y axis in both FIGS. 4A and 4B represents the total aligned sequencing counts of the libraries.

FIGS. 5A and 5B represent number of the concentrations of the libraries.

FIG. 7 shows an exemplary configuration of an adaptor-ligated double stranded nucleic acid from a library. In this embodiment, both the P5 and P7 adaptor comprise sample indexes, located in positions indicated by [i5] and [i7], respectively. FIG. 7 discloses SEQ ID NOS 18, 19, 14, 15, 12, 17, 20, 21, 18, 19, 14, 15, 12, 17, 20, and 21, respectively, in order of appearance.

FIG. 8 discloses SEQ ID NOS 1, 14, 15, 12, 17, 16, 1, 14, 15, 12, 17, and 16, respectively, in order of appearance.

FIG. 9 shows two exemplary probes that can be used with the capNorm method. Also shown in FIG. 9 are hybridization complexes formed by the probes and two complementary single stranded nucleic acid molecules from a library. FIG. 9 discloses SEQ ID NOS 3, 4, 1, 14, 15, 4, 3, 12, 17, and 16, respectively, in order of appearance.

DETAILED DESCRIPTION OF THE INVENTION

Figure 2A:
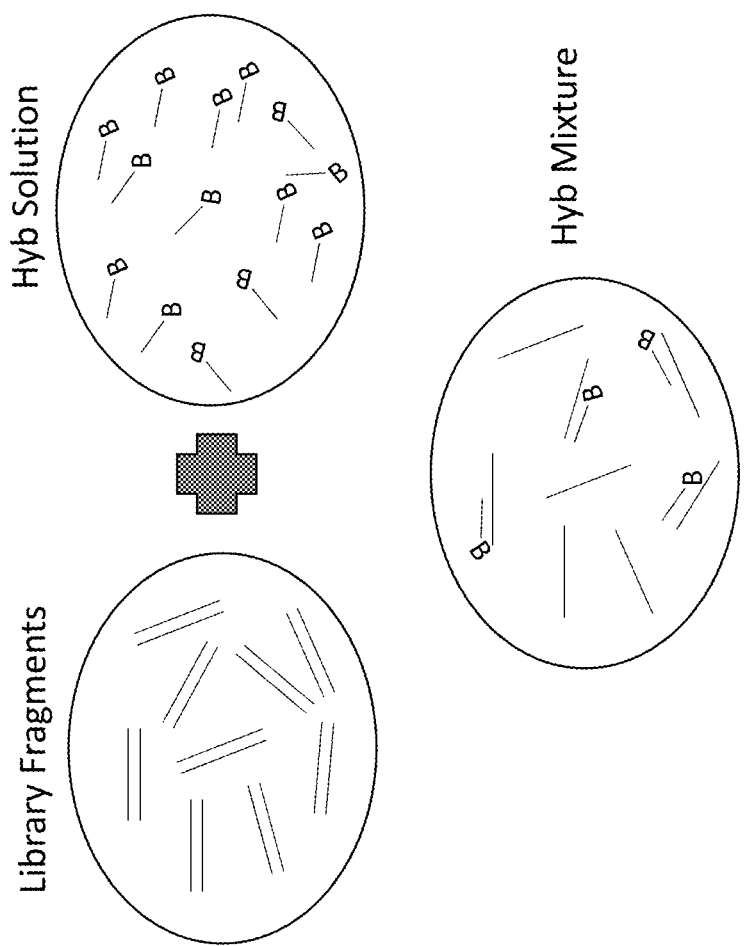

The present invention relates generally to methods of normalizing nucleic acid libraries. The double stranded nucleic acid molecules in the libraries are ligated to adaptors (e.g., a P5 adaptor at one end and a P7 adaptor at the other end) that are configured to facilitate analyzing the molecule features of nucleic acid libraries by downstream assays, for example, sequencing. Nucleic acid probes with nucleic acid sequences that are complementary to one or more of these adaptor sequences are added to the nucleic acids libraries. The mixture is heated so that the two complementary strands of the double stranded nucleic acid molecules in the libraries become separated to form single stranded nucleic acid molecules, and the probes can hybridize to the adaptor sequences in the single stranded nucleic acid molecules to form hybridization complexes. The probes are conjugated to a first binding member, which can interact with a second binding member that is conjugated to solid supports. Hybridization complexes are contacted with the solid supports and become bound to the solid supports via the interaction between the two binding members. The solid supports can then be collected and the single stranded nucleic acid molecules can be recovered in a volume of elution buffer to reach a desired concentration. The methods collectively are referred to as capNorm in this disclosure.

CapNorm can be automated and parallelized, i.e., it can be used to simultaneously normalize a large number of libraries, for example, within a 96-well reaction plate using a standard liquid handler. capNorm uses less steps than the conventional normalization method, thus can be performed faster. For example, instead of performing purification, quantitation and volume-based normalization in three steps that take a combined 4 hours, capNorm uses one step that can be completed within 1.5 hours. By using similar amount of probes and beads to capture the single stranded nucleic acid molecules and similar amount of elution buffer to recover the single stranded nucleic acid molecules, the variation between concentrations of nucleic acid molecules recovered from libraries are reduced, thus achieving the objective of normalization. In addition, because capNorm includes the binding and washing of the nucleic acid molecules from the libraries, it can be used directly on the PCR amplified materials, which makes standard post-PCR cleanup step unnecessary. The normalized nucleic acid libraries can be used for many downstream assays, including but not limited to, sequencing, target capturing, and amplification.

Definitions

The terms "nucleic acid molecules" refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracrRNAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The term "nucleic acid sequence" as used herein refer to the sequence of a nucleic acid molecule. The nomenclature for nucleotide bases as set forth in 37 CFR § 1.822 is used herein.

As used herein, the term a "nucleic acid sample" refers to a collection of nucleic acid molecules. In some embodiments, the nucleic acid sample is from a single biological source, e.g., one individual or one tissue sample, and in other embodiments the nucleic acid sample is a pooled sample, e.g., containing nucleic acid molecules from more than one organism, individual or tissue.

The term "nucleic acid sample" encompasses "nucleic acid library" which, as used herein, includes a nucleic acid library that has been prepared by any method known in the art. In some embodiments, providing the nucleic acid library includes the steps required for preparing the library, for example, including the process of incorporating one or more nucleic acid samples into a vector-based collection, such as by ligation into a vector and transformation of a host. In some embodiments, providing a nucleic acid library includes the process of incorporating a nucleic acid sample into a non-vector-based collection, such as by ligation to adaptors. In some embodiments, the adaptors can anneal to PCR primers to facilitate amplification by PCR or can be universal primer regions such as, for example, sequencing tail adaptors.

The term "A adaptor" and "B adaptor" refer to two adaptors that are ligated to the ends of the double stranded nucleic acid molecules, one at each end. The A adaptor and B adaptor referred to herein can comprise any common sequences that are shared by the libraries to be normalized, to which the probes of the disclosure can be designed to hybridize. These adaptors are employed to assist the downstream analysis of their molecule features. In some cases the A adaptor may be a P5 adaptor and the B adaptor may be a P7 adaptor. Although the exemplary adaptors, P5 and P7, are used to describe various embodiments of the disclosure, any adaptors suitable for next gen sequencing may be used. The A adaptor may be a double-stranded adaptor comprising an A adaptor sequence and an A' adaptor sequence, which are complementary to each other. Similarly, the B adaptor may be a double-stranded adaptor comprising a B adaptor sequence and a B' adaptor sequence, which are complementary to each other.

"Washing" with respect to washing a solid support, e.g., a bead, means reducing the amount and/or concentration of one or more substances in contact with the solid support or exposed to the solid support. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a volume of liquid in contact with a magnetically responsive solid support, where the liquid includes an initial amount and initial concentration of a substance. The washing operation may yield a volume of liquid including the magnetically responsive bead, which is less than the initial amount and/or concentration of the substance. Examples of suitable washing techniques are described in Pamula et al., U.S. Pat. No. 7,439,014, entitled "Droplet-Based Surface Modification and Washing," issued on Oct. 21, 2008, the entire disclosure of which is incorporated herein by reference.

The term "do not significantly overlap" with regard to two nucleic acid sequences refers to that they do not share more than 3, more than 4, more than 5, more than 6, more than 7, more than 8, more than 9, or more than 10 consecutive complementary nucleotides. An example is shown in FIG. 9, in which the two capture probes BioTinTEG-ILMN_P5f and BioTinTEG-ILMN_P5rc do not significantly overlap and share 7 consecutive complementary nucleotides.

The term "comparable" or "similar" when regard to two values (e.g., CV or the amount of probes, or the amount of beads), refers to that the difference between the two values are no greater than 10%, no greater than 8%, no greater than 7%, or no greater than 5%, no greater than 2%, no greater than 1%, based on the smaller of the two values.

The term "complementary" refers to the capacity for precise pairing between two nucleotides. For example, if a nucleotide at a given position of a nucleic acid is capable of hydrogen bonding with a nucleotide of another nucleic acid, then the two nucleic acids are considered complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably.

The terms "hybridization" and "hybridizing" refer to base pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used. In the present invention, the term "hybridization" refers particularly to hybridization of a probe to the library to be normalized.

The term "library" or "nucleic acid library" refers to a set of nucleic acid molecules (circular or linear) representative of all or a significant portion of the nucleic acid content of a defined sample, e.g., a cell, a tissue, a blood-based sample (e.g., serum or plasma), organ, or organism as discussed in more detail herein.

The term "normalized" or "normalized library" means a nucleic acid library of a plurality of nucleic acid libraries that have been manipulated, preferably using the methods of the invention, to reduce the relative variation in concentration among member nucleic acid libraries. Relative variation can be measured by comparing the highest concentration in the range versus the lowest concentration in the range. In some cases, the relative variation in concentration among the normalized libraries is reduced to a range of no greater than about 8-fold, no greater than about 7-fold, no greater than about 6 fold, no greater than about 5-fold, no greater than about 4-fold, no greater than about 6-fold, no greater than about 5-fold, no greater than about 4-fold, no greater than about 3-fold or no greater than about 2-fold. In some cases, the coefficient of variation of the concentrations of the normalized libraries are less than 25%, less than 22%, or less than 20%. The coefficient of variation (CV) reflects a measure of dispersion scaled by the mean value. It is typically calculated by dividing the standard deviation of a dataset by the mean of the dataset. It can then be multiplied by 100 and reported as a percentage.

The term "pre-normalized" or "pre-normalized library" refers to libraries that have not been manipulated to reduce the relative variation in concentration among member nucleic acid libraries. The term "pre-normalized range" refers to the range of the measurements (e.g., concentrations) of pre-normalized libraries. The term "normalized range" refers to the range of measurements (e.g., concentrations) of libraries that have been normalized.

The term "total aligned sequencing counts" refers to the number of sequence reads (per sample) that align to the human reference genome. It is the number of sequence reads whose chromosomal location in the human genome can be identified.

The term "comprising" is synonymous with "including," "containing," and is inclusive or open-ended and does not exclude additional, unrecited elements or method steps. As used herein, "consisting of" excludes any elements, steps, or ingredients not specified in the claimed composition or method. As used herein, "consisting essentially of" does not exclude materials or steps that do not materially affect the basic and novel characteristics of the claimed composition or method. Any recitation herein of the term "comprising", particularly in a description of components of a composition or in a description of steps of a method, is understood to encompass those compositions and methods consisting essentially of and consisting of the recited components or steps.

Unless explicitly stated to the contrary, all concentrations referred to this disclosure refer to molar concentrations.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges, which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Other terms used in the fields of recombinant DNA technology and molecular and cell biology as used herein will be generally understood by one of ordinary skill in the applicable arts.

Nucleic Acid Libraries

CapNorm can be performed on nucleic acid libraries prepared from any biological sources. The nucleic acids libraries can be prepared from natural sources, such as a variety of cells, tissues, organs or organisms. Cells that may be used as sources of nucleic acid molecules may be prokaryotic or eukaryotic, plants, protozoans and other parasites, and animals including insects (e.g., *Drosophila* spp. cells), nematodes (e.g., *Caenorhabditis elegans* cells), and mammals (particularly human cells)).

Mammalian somatic cells that may be used as sources of populations or libraries of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids or libraries for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above prokaryotic or eukaryotic cells, tissues and organs may be normal, diseased, transformed, established, progenitors, precursors, fetal or embryonic. Diseased cells may, for example, include those involved in infectious diseases (caused by bacteria, fungi or yeast, viruses (including HIV) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, F9 cells and the like. Other cells, cell lines, tissues, organs and organisms suitable as sources of nucleic acids for use in the present invention will be apparent to one of ordinary skill in the art. These cells, tissues, organs and organisms may be obtained from their natural sources, or may be obtained commercially from sources such as American Type Culture Collection (Rockville, Md.) and others that are known to the skilled artisan.

In some cases, each nucleic acid library comprises populations of nucleic acid molecules derived from an individual patient. The nucleic acid libraries that can be normalized using capNorm may include populations of single stranded or double stranded nucleic acid molecules. In some cases, the pre-normalized concentration of the double stranded library may range from 15 to 200 nM, e.g., from 20 to 180 nM, from 40 to 150 nM.

Methods of isolation of nucleic acid molecules (such as mRNA or poly A+ RNA) from one or more biological sources above and preparation of nucleic acid libraries therefrom, are well-known in the art (See, e.g., Maniatis, T., et al., Cell 15:687-701 (1978); Okayama, H., and Berg, P., Mol. Cell. Biol. 2:161-170 (1982); Gubler, U., and Hoffman, B. J., Gene 25:263-269 (1983)). As noted above, nucleic acid libraries prepared in such a manner will typically contain a vast range of abundances of member nucleic acid molecules, depending upon the cell, tissue or organism source, and the stage of development or cell cycle of the source. The methods of the invention may then be used to normalize these nucleic acid libraries.

Workflow to Prepare Libraries before Normalization

The typical workflow to prepare the nucleic acid library includes end repair of the DNA fragments, ligation with adaptors configured to facilitate the downstream biochemical assays, purification of the adapter-ligated fragments and then PCR amplification. Double stranded nucleic acid molecules are denatured to prepare single stranded nucleic acids library for the CapNorm methods.

Methods for end repair are well known. In some cases, the ends of a DNA fragment can be repaired, or blunted, via 5' to 3' polymerase activity and 3' to 5' exonuclease activity, and then the 5' end of the DNA fragment is phosphorylated and then 3) a single nucleotide overhang is added to the 3' end. For example, a nucleotide "A" may be added to provide a binding partner to the T-tailed adapter for 'sticky' or cohesive-end ligation.

Figure 8:
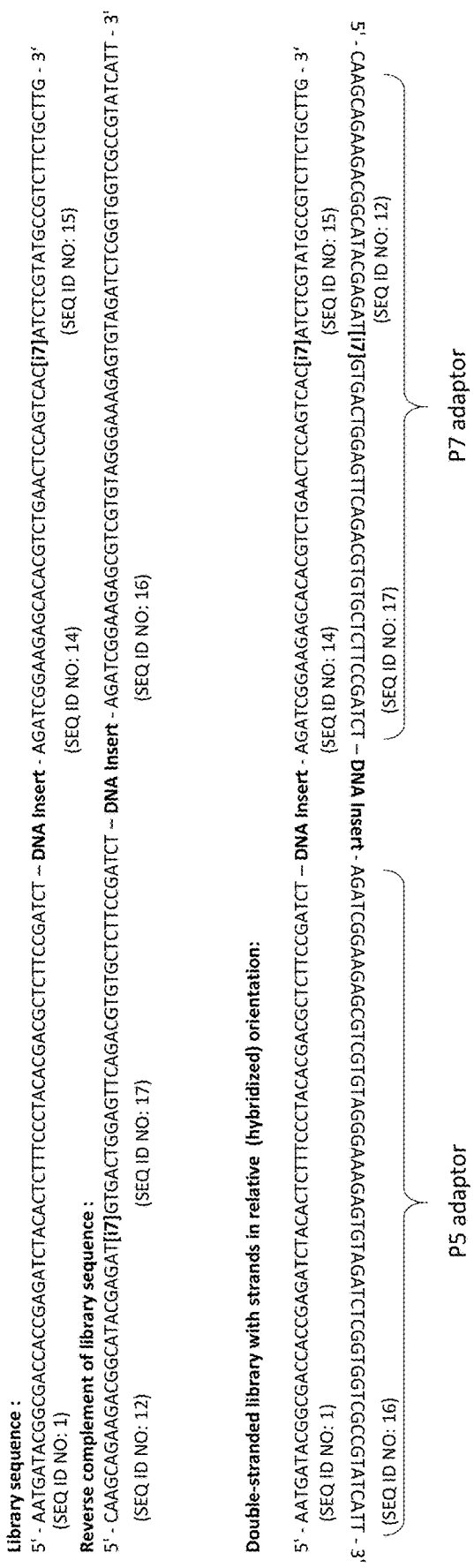
FIG. 8 shows another exemplary configuration of an adaptor-ligated double stranded nucleic acid library. This configuration is the same as the one shown in FIG. 7, except that only the P7 adaptor comprises a sample index, located in a position as indicated by [i7].

After the end repair, double stranded nucleic acid molecules are ligated with double stranded adaptors, A and B, one at each end under ligating conditions. A and B adaptors can comprise any sequences that are shared among the member libraries and can facilitate analysis of the molecular features of the libraries. In some cases, the A and B adaptors can be adaptors used for sequencing in any sequencing platform In some cases, the A and B adaptors are P5 and P7 adaptors, which contain sequences specific for sequencing on the Illumina platforms. In some cases, the adaptors comprise sequences that can hybridize to the oligos in the flow cell of the sequencer. In some cases, the P5 adaptor comprises a P5 sequence of SEQ ID NO: 10 (5'-AATGA-TACGGCGACCACCGAGA-3') and its complementary sequence P5' SEQ ID NO: 11 (5'-TCTCGGTGGTCGCCGTATCATT-3'). The P7 adaptor comprises a P7 sequence of SEQ ID NO: 12 (5'-CAAGCAGAAGACGGCATACGAGAT-3') and its complementary sequence P7', SEQ ID NO: 13 (5'-ATCTCGTATGCCGTCTTCTGCTTG-3'). In some cases, one strand of the double stranded nucleic acid that is ligated with the P5 and P7 adaptors may comprise a P5 sequence and a P7' sequence at two ends and the other strand comprises a P7 sequence and a P5' sequence at two ends. Examples of adaptor-ligated double stranded nucleic acid molecules are shown in FIG. 7 and FIG. 8. FIG. 7 and FIG. 8 show double stranded nucleic acid molecules that have been ligated with an exemplary P5 adaptor at one end and an exemplary P7 adaptor at the other end. The sequences of the two complementary strands of the P5 adaptor are referred to as the P5 adaptor sequence and the P5' adaptor sequence. Similarly, the sequences of the two complementary strands of the P7 adaptor are referred to as the P7 adaptor sequence and the P7' adaptor sequence. The adaptors ligated to the ends of the nucleic acid molecules in the libraries typically have a length that ranges from 50 to 80 base pairs, e.g., from 52 to 75 base pairs, from 55 to 70 base pairs, or 58 to 65 base pairs.

In some embodiments, either strand of the A adaptor (e.g., the P5 adaptor) or the B adaptor (e.g., the P7 adaptor) may further comprises a sample index (index 1 primer or index 2 primer), a sequencing primer (e.g., read1 primer or read2 primer), a PCR primer sequence, or a combination thereof. For example, the double stranded nucleic acid molecule in FIG. 7 comprises two sample indexes, one in the P5 adaptor and the other in the P7 adaptor; and their positions in the adaptors are indicated by [i5] and [i7], respectively. The double stranded nucleic acid molecule in FIG. 8 contains one sample index in the P7 adaptor, in the position where indicated by [i7]. In some cases, the index is a sample index, used to identify the source of the nucleic acid molecule. For example, all nucleic acid molecules in each library can be tagged with a same unique sample index.

In some embodiments, the P5 adaptor sequence comprises SEQ ID NO: 1 (5'-AATGATACGGCGACCACCGAGATC-TACACTCTTTCCCTACACGACGCTCTTCCGATCT-3'). In one embodiment, the P7 adaptor sequence comprises SEQ ID NO: 14 and SEQ ID NO: 15 (5'-AGATCG-GAAGAGCACACGTCTGAACTCCAGTCAC[i7] ATCTCGTATGCCGTCTTCTGCTTG-3'). [i7] represents the position of a sample index sequence, located between a nucleic acid sequence of SEQ ID NO: 14 (5'-AGATCG-GAAGAGCACACGTCTGAACTCCAGTCAC-3') and a nucleic acid sequence of SEQ ID NO: 15 (5'-ATCTCGTATGCCGTCTTCTGCTTG-3') in the P7 adaptor. The adaptor ligated- nucleic acid molecules in the libraries can then be amplified using primers that anneal to the PCR primer sequences on the adaptors.

CapNorm

CapNorm uses probes that can hybridize to the adaptor sequences in the nucleic acid molecules in the libraries. The nucleic acid molecules are captured using solid supports that can bind to the probes. After washing the solid supports, the captured nucleic acid molecules are eluted. The concentration of the libraries are normalized by adding the same amount of probes and the same amount of solid supports to each library. Unlike the standard method as disclosed in FIG. 1A, which is only conducted on amplified nucleic acid libraries that have been purified to remove the unincorporated amplification primers, capNorm can be performed directly on amplified nucleic acid libraries, without the need to purify the amplified libraries. CapNorm can also be performed on the nucleic acid libraries that have been purified to remove primers. As compared to the standard method as disclosed in FIG. 1A, the capNorm, illustrated in FIG. 1B, combines the three steps, i.e., purification, quantitation, and volume-based normalization into one step, which significantly shortens the time required for preparing the libraries for downstream assays.

In general, the capNorm method comprises adding a hybridization solution to the nucleic acid libraries. The hybridization solution comprises probes with sequences that are complementary to the adaptors. In some cases, the nucleic acids libraries are single stranded, and the probes will hybridize to the adaptor sequences on the single stranded nuclei acid molecules. If the nucleic acids are double stranded, the double stranded nucleic acid (and optionally, the hybridization buffer) libraries are first denatured to form single stranded nucleic acid molecules, which will then hybridize to the probes (FIG. 2A). The libraries can be denatured by heating the mixture at a high temperature (e.g., about 100-120° C., or about 107.5° C.) for a time period, for example, from 3 to 10 minutes, e.g., about 5 minutes. The reaction is then cooled at room temperature to hybridize the probes to the denatured, single stranded nucleic acid molecules.

Figure 2C:
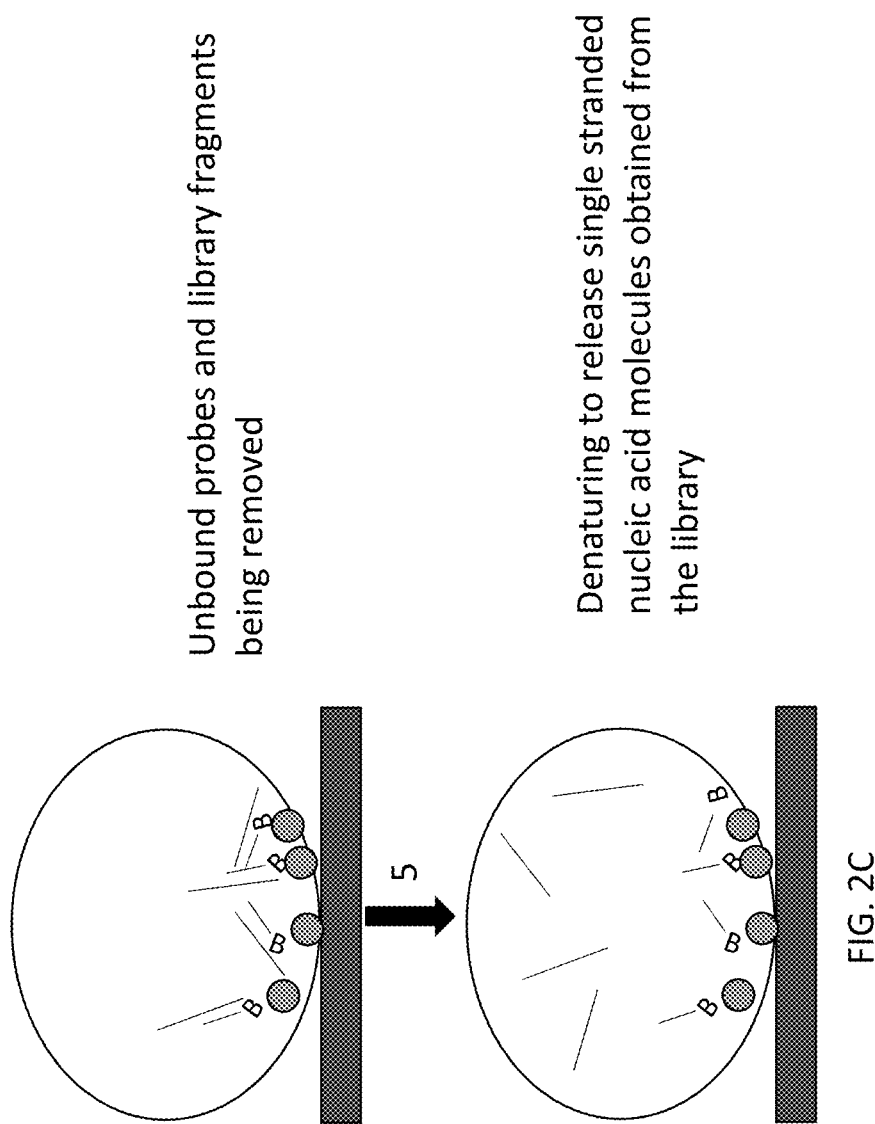

The probes are conjugated to a first binding member, which can bind to solid supports that are conjugated to a second binding member. Solid supports conjugated to a second binding member are subsequently used to capture the hybridization complexes (FIG. 2B). The solid supports that are bound with hybridization complexes are then collected, and washed to remove unbound probes and nucleic acid molecules (FIG. 2C). The solid supports are then resuspended in an elution buffer and heated to denature the hybridization complex, which results in the single stranded nucleic acid molecules being separated from the probes they bind. Because the amount of beads and elution buffer can be controlled in capNorm, the concentrations of the single stranded nucleic acid molecules from the libraries after capNorm can be normalized within a predictable range that is suitable for downstream applications, see below. This method can be parallelized to normalize a large number of libraries to produced normalized number of libraries by using the same amount of probes and the same amount of solid supports to process each library.

Hybridization Solution

The hybridization solution used in capNorm comprise probes and salts (e.g., sodium chloride), buffers (e.g., Tris- HCl), surfactants (e.g., Tween 20), and other reagents that can facilitate the hybridization of the probes to the adaptors. The salts may be present in a concentration that ranges from 75 to 1200 mM, e.g., from 150 to 1200 mM, from 400 to 1000 mM, or from 450 to 900 mM, or about 375 mM.

Probes

The probe may comprise sequences that are complementary to the P5 adaptor sequence, the P7 adaptor sequence, the P5' adaptor sequence, or the P7' adaptor sequence. The probes are designed to have a melting temperature of between the room temperature (about 22° C.) and the denature temperature (greater than 100° C.). In some cases, the melting temperature ranges from 40 to 80° C., e.g., from 50 to 70° C., from 55 to 65° C., or about 60° C. The probes typically have a length that ranges from 18 to 35 nucleotides, e.g., from 20 to 30 nucleotides, or from 23 to 27 nucleotides.

The concentration or the amount of the probes in the hybridization solution may vary. The concentration of the probes may be determined based on the concentration or amount of the pre-normalized libraries, yield requirement (e.g., the amounts of the normalized libraries required for downstream assays), salt concentration in the hybridization solution, and so on. In general, sequencing based assays can be performed using very low amounts of library materials, whereas target capture assay may require higher yield. It has been found that increasing concentration of the probes may increase yield but could also increase variability of the concentrations of the normalized libraries. Thus, it is desirable to maintain the total probe concentrations within appropriate ranges. In some embodiments, the concentration of the probes may range from 10 to 500 nM, e.g., from 15 to 200 nM, from 20 to 100 nM, or about 25 nM. In some embodiments, the ratio of the molar amount of the probes to the molar amount of the single nucleic acid molecules from the pre-normalized library ranges from 0.025:1 to 16.7:1, e.g., from 0.025:1 to 10:1, from 0.025:1 to 1:1, from 0.03:1 to 0.9:1, or from 0.03:1 to 0.8:1.

The adaptors added to the end of the nucleic acid libraries often comprise functional sequences (e.g., a sample index sequence, a P5 sequence, or a P7 sequence) that facilitate the downstream biochemical analysis. In some cases, when capNorm is performed directly on amplified nucleic acid libraries, which may still contain unbound primers, probes are typically designed such that they do not significantly overlap with the sequence of the PCR primers; this can avoid hybridization between the probes and the PCR primers, which would deplete the probes that could otherwise hybridize to the nucleic acid libraries. CapNorm methods using probes designed with one or more of these considerations can advantageously produce normalized nucleic acid libraries with high yield and minimize negative effects on the efficiency of the downstream assays.

Table 1 shows exemplary probes that can be used in capNorm to normalize the nucleic acid libraries for next generation sequencing:

TABLE 1

Exemplary Probes Sequences

| SEQ ID NO | Name | Probe Seq | Basic Tm | Size (nt) |
|---|---|---|---|---|
| 3 | P5f | 5'-CCT ACA CGA CGC TCT TCC GAT CT-3' | 58.8 | 23 |
| 4 | P5rc | 5'-GTG TAG GGA AAG AGT GTA GAT CTC GGT-3' | 59.7 | 27 |
| 5 | P5rc2 | 5'-GTG TAG ATC TCG GTG GTC GCC-3' | 58.3 | 21 |
| 6 | P7rc1 | 5'-TGA CTG GAG TTC AGA CGT GTG CTC-3' | 59.1 | 24 |
| 7 | P7rc2 | 5'-CAA GCA GAA GAC GGC ATA CGA GAT-3' | 57.4 | 24 |
| 8 | P7rc3 | 5'-GTT CAG ACG TGT GCT CTT CCG ATC-3' | 59.1 | 24 |
| 9 | P7rc4 | 5'-CTG GAG TTC AGA CGT GTG CTC TTC-3' | 59.1 | 24 |

Hybridization between the Probe and Single Stranded Nucleic Acid Molecules from the Libraries There are a number of configurations where probes can hybridize to the single stranded nucleic acid molecules. In some embodiments, the probes are hybridized to both strands of the complementary strands of the nucleic acid molecules. Such as described in FIG. 3A-3E. In some embodiments, the probes are hybridized to only one strand of the two complementary strands, such as FIGS. 3F, 3G, 3H, and 3I. CapNorm methods that utilize probes to hybridize and capture both strands of the two complementary strands may produce normalized libraries with higher yield than those that only hybridize and capture only one of the two complementary strands.

Figures 3A, 3B, 3C:
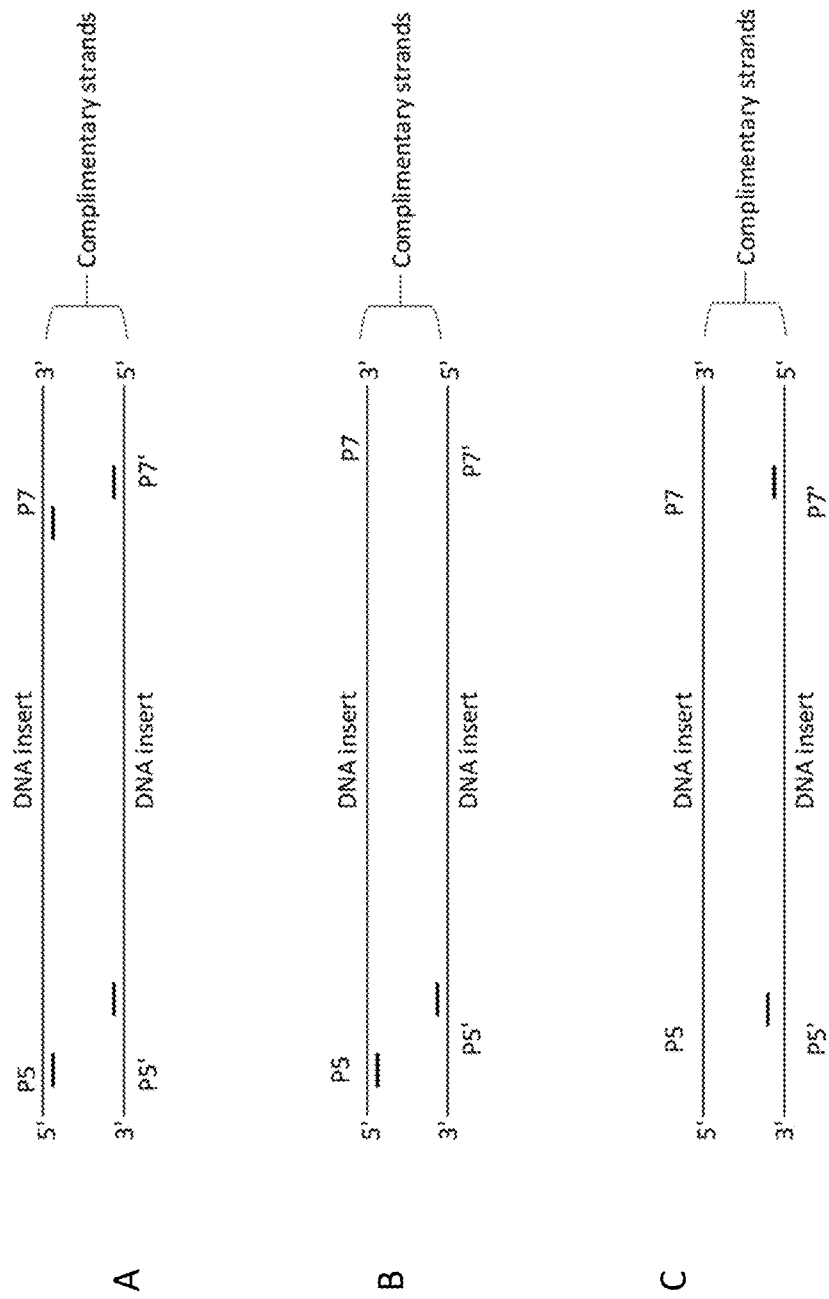
FIG. 3A-3E show the exemplary configurations where probes are hybridized to both complementary single stranded nucleic acid molecules. These single stranded nucleic acid molecules are formed when the double stranded nucleic acid were denatured.
Figures 3D, 3E:
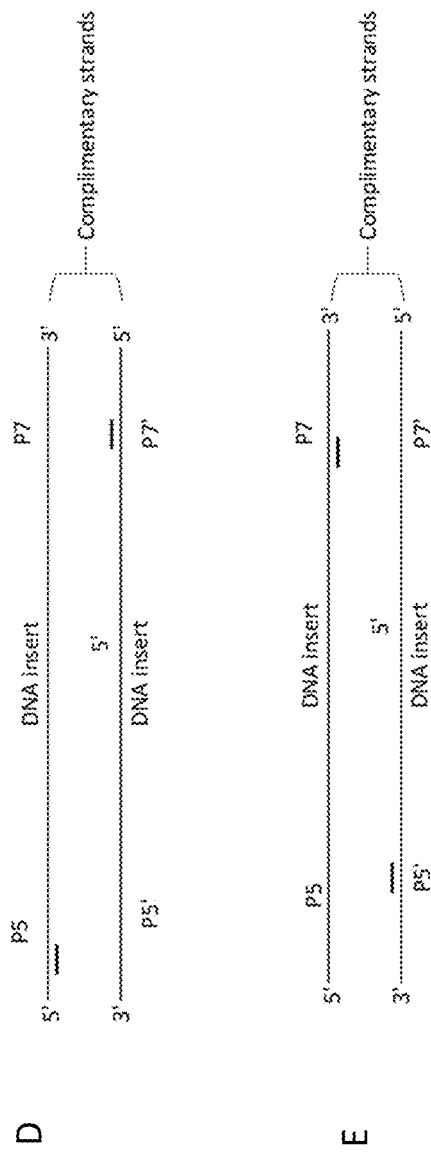
Figures 3F, 3G, 3H:
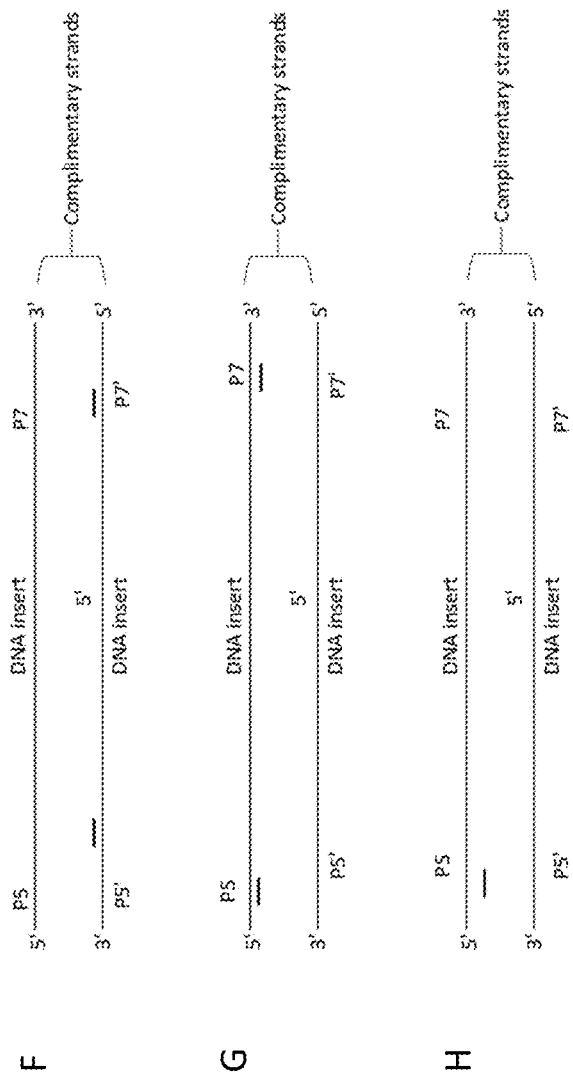
FIG. 3F-3K show exemplary configurations where probes are hybridized to one of the complementary single stranded nucleic acid molecules.
Figures 3I, 3J, 3K:
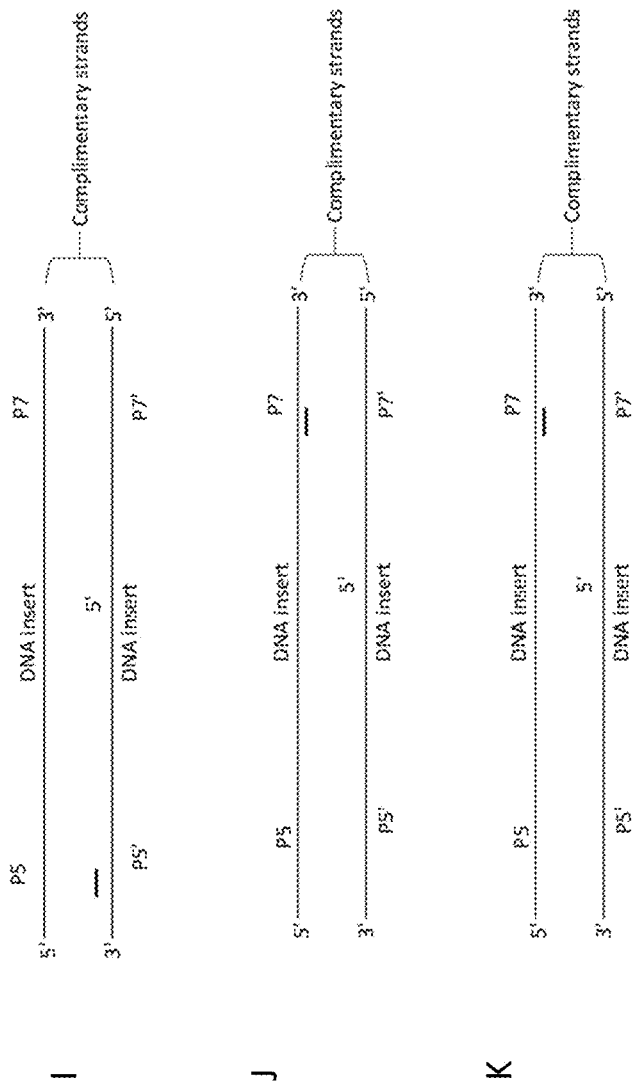

In some embodiments, each single stranded nucleic acid molecule is hybridized to one probe, as shown in FIG. 3C. In some embodiments, each single stranded nucleic acid is hybridized to two or more probes, as shown in FIG. 3A. In FIG. 3A-3I, P5, P5', P7, and P7' represent the P5 adaptor sequence, the P5' adaptor sequence, the P7 adaptor sequence, and the P7' adaptor sequence.

Binding Member

Probes used in capNorm are conjugated to a first binding member, which can bind to a second binding member that is conjugated to a solid support. The interaction between the two binding members ("a binding pair") results in the capture of the nucleic acid molecules from the libraries on the solid supports.

Binding pairs are well known in the art. In some cases, the binding pair can consist of an antigen and an antibody that can bind to the antigen. In some cases, the binding pair can consist of a receptor and a ligand. In some cases, the binding pair can consist of an enzyme and an inhibitor of the enzyme. In some cases, the binding pair can consist of an enzyme and its co-factor. Specific examples of such specific binding pairs include, but are not limited to, carbohydrate and lectin, biotin and avidin or streptavidin or NeutrAvidin, amine-modified oligos and carboxylate, folic acid and folate binding protein, vitamin B12 and intrinsic factor, protein A and immunoglobulin, and Protein G and immunoglobulin. The first binding member can be either member of the binding pairs described above. Either member of a binding pair can be the first binding member or the second binding member. For example, a binding pair may comprise a first binding member that is biotin and a second binding member that is streptavidin. A binding pair may comprise a first binding member that is streptavidin and a second binding member that is biotin.

In some cases, a probe used in capNorm may comprise a spacer between the first binding member and the first nucleotide of the probe. The spacer can advantageously minimize steric hindrance that may occur during the binding and capture procedure. In some cases the spacer is a chemical compound that has a carbon chain, which has a length ranging from 2 to 7, e.g., from 3 to 6 carbons. In some cases, the spacers are phosphoramidites. In some cases the spacer is a chemical compound that has a carbon chain, which has a length ranging from 2 to 13, e.g., from 3 to 12 carbons, or multiples thereof. In some cases, the spacer is an ethylene glycol including tri-, hexa-, or tetra-ethylene glycol.

In some embodiments, the probes used in the capNorm comprise BioTinTEG-ILMN_P5f, which has a sequence of 5'-BioTinTEG-CCTACACGACGCTCTTCCGATCT-3' (SEQ ID NO: 3). In some embodiments, the probes comprise BioTinTEG-ILMN_P5rc, which has a sequence of 5'-BioTinTEG-GTGTAGGGAAAGAGTGTA-GATCTCGGT-3' (SEQ ID NO: 4). In some embodiments, the probes comprise both BioTinTEG-ILMN_P5f and BioTinTEG-ILMN_P5rc. FIG. 9 illustrates the formation of the hybridization complexes between these probes and two complementary single stranded nucleic acid molecules.

Solid Support

The solid support used in the methods and compositions of the invention are conjugated to a second binding member that can bind to the first binding member conjugated to the probes. The interaction between the first and second binding members allows the solid supports to capture the probes that are hybridized to the single stranded nucleic acid molecules derived from the nucleic acid libraries. Solid supports used in capNorm can take a number of different forms. In some cases, the solid supports are substantially planar (e.g., slides, plates). In some cases, the solid supports are nonplanar and unitary or formed from a plurality of distinct units (e.g., beads). A solid support may comprise a discrete particle that may be spherical or have a non-spherical or irregular shape, such as cubic, cuboid, pyramidal, cylindrical, conical, oblong, or disc-shaped, and the like. A solid support may encompass any type of solid, porous, or hollow sphere, ball, bearing, cylinder, or other similar configuration composed of plastic, ceramic, metal, or polymeric material (e.g., hydrogel) onto which a binding member may be attached (e.g., covalently or non-covalently). In some embodiments, the solid support can be a Pellet MyOne streptavidin C1 bead plate, which comprise 10 ul beads @ 10 mg/ml.

In some cases, the solid supports comprise paramagnetic materials. Paramagnetic materials are responsive to a magnetic field. Examples of suitable paramagnetic materials include iron, nickel, and cobalt, as well as metal oxides, such as $Fe_3O_4$, $BaFei_2O_i9$, $CoO$, $NiO$, $Mn_2O_3$, $Cr_2O_3$, and $CoMnP$. Paramagnetic solid supports (e.g., paramagnetic beads) that are bound with hybridization complexes can be collected by placing the mixture in a magnetic field.

The amount of solid supports used for each capNorm reaction may vary. In general, increased quantity of the solid supports can increase the yield of the normalized library, however, this also increases the cost of capNorm. Thus it is desirable to use as many solid supports as necessary to capture as many of the hybridization complexes as possible. The quantity of the solid supports used for normalizing each library is determined based on a number of factors, including the probe concentration, the number of probes used in each hybridization complexes, and the number of second binding members attached to each solid support. The optimal number of the solid supports used for each reaction can be determined empirically. In some embodiments, the ratio of the number of the solid supports to the number of the probes used for the capture is 1:1 to 1:100, In some cases, the amount of solid supports ranges from 10 to 1000 μg, e.g., from 20 to 800 μg, from 40 to 700 μg, from 50 to 600 μg, or about 200 μg per reaction.

The collected solid supports are washed and supernatants from each wash are discarded. The wash step may be repeated to remove the unbound materials. An elution buffer is added to the solid supports, and the mixture heated to a temperature that is sufficiently high (e.g., 80-90° C.) to denature the hybridization complexes. Once denatured, the single stranded nucleic acid molecule is separated from the probe and released into the eluate and collected, which forms a normalized nucleic acid library.

The methods disclosed herein can be used to conveniently normalizing a plurality of nucleic acid libraries which are of different concentrations in a pre-normalized range. Single stranded nucleic acid molecules from each library are hybridized with a predetermined amount of probes to form hybridization complexes. The single stranded nucleic acid molecules each comprise an A adaptor sequence and a B adaptor sequence, or an A' adaptor sequence and a B' adaptor sequence. The A adaptor sequence is a reverse complement of the A' adaptor sequence and the B adaptor sequence is a reverse complement of the B' adaptor sequence. Each hybridization complex comprises one of the single-stranded nucleic acid molecules and one or more probes, each of which has a sequence that is complementary to the A adaptor sequence, the B adaptor sequence, the A' adaptor sequence, or the B' adaptor sequence. The one or more probes each is conjugated to a first binding member. The method further comprises contacting the hybridization complexes formed by the single stranded nucleic acid molecules of each library and the probes with a predetermined amount of solid supports. Each solid support is conjugated to a second binding member, which binds to the first binding member on the probes, resulting in the solid supports binding to the hybridization complexes to form solid support-bound hybridization complexes. The solid support-bound hybridization complexes are then collected and single stranded nucleic acid molecules are separated from the probes to obtain a normalized library. This results in a plurality of normalized libraries of different concentrations in a normalized range, and the normalized range is narrower than the pre-normalized range. The plurality of normalized nucleic acid libraries can be pooled for downstream assays.

Optionally, the concentrations of the normalized libraries can be determined, and the relative variation in concentration among the normalized libraries are calculated to verify the normalization of the libraries according to predetermined criteria. CapNorm can reduce the relative variation in concentrations, i.e., the normalized concentration range is narrower than the pre-normalized range. The CV of the concentrations of the normalized libraries are typically less than 25%. In some cases, the relative variation in concentration among the normalized libraries is no greater than 8 fold, no greater than 7 fold, no greater than 6 fold, no greater than 5 fold, no greater than 4 fold, no greater than 3 fold, e.g., no greater than 2 fold. In some cases, the range of relative variation in concentration of normalized libraries is narrower by at least 30% as compared to the range of relative variation in concentration of pre-normalized libraries, for example, at least 50%, at least 60%, or at least 80%.

Reaction Mixtures and Kits

This disclosure also provides a reaction mixture comprising a hybridization solution and single stranded nucleic acid molecules derived from a nucleic acid library. The hybridization solution may comprise one or more probes and a salt, wherein one or more probes each have a sequence that is complementary to the A adaptor sequence, the B adaptor sequence, the A' adaptor sequence, or the B' adaptor sequence, wherein the one or more probes, each conjugated to a first binding member. In some embodiments, the reaction mixture further comprises a solid support, e.g., a paramagnetic bead.

Also provided herein is a kit comprising (i) probes each have a sequence that is complementary to the A adaptor sequence, the B adaptor sequence, the A' adaptor sequence, or the B' adaptor sequence, and (ii) a paramagnetic solid support, wherein the solid support is conjugated to a second binding member, and wherein the first binding member is capable of binding to the second binding member.

Sequencing

In some embodiments, the nucleic acid libraries normalized using capNorm are pooled for sequencing. In some embodiments, the normalized libraries disclosed herein may be amplified prior to sequencing. Any suitable sequencing method known in the art can be used, preferably high-throughput approaches. For example, cyclic array sequencing using platforms such as MiSeq, Roche 454, Illumina Solexa, ABI-SOLiD, ION Torrent, Complete Genomics, Pacific Bioscience, Helicos, or the Polonator platform, may also be utilized. In some embodiments, sequencing may comprise Solexa sequencing.

The normalization of the nucleic acid libraries can be further verified by the coefficient of variation (CV) of the total aligned sequencing counts from the individual nucleic acids libraries. The total aligned sequencing counts is the number of sequence reads (per library) which align to the human reference genome and they represent the number of sequence reads whose chromosomal location in the human genome can be identified. capNorm has been shown to be able to significantly reduce the variability of total aligned sequencing counts and the CV of the total aligned sequencing counts is typically less than 25%, less than 22%, less than 18%, or less than 16%. In one illustrative example, as shown in Example II and FIG. 5, the CV of the total aligned sequencing counts of the libraries was reduced from 43% (non-normalized libraries) to 15% (normalized libraries). Example III and FIG. 6 show that the capNorm can effectively normalize the libraries to a similar degree as the standard method—the CV of the total aligned sequence counts among libraries normalized using both methods were comparable: being 14.5% and 15.7%, respectively, and both well below the target value of 25%.

It will be appreciated that normalizing libraries prior to sequencing can increase the number of sequencing reads (i.e., sequencing counts) for intermediate or low libraries in the pool, and/or decreasing the number of sequencing reads for high concentration libraries in the pool. A low CV of the total aligned sequencing counts is an indication that the sequencing reaction is accurate and efficient. This is because for a sequencing-based test, an accurate result requires a sufficient number of properly aligned high quality reads/counts per patient sample (the actual number is test-specific). A wide variation in the total aligned sequence counts of the patient libraries will result in the undesired consequence, where some patient samples will yield far more reads than is necessary for the test while others will not generate enough reads and will fail QC metrics. Normalizing the libraries using the capNorm methods as disclosed herein prior to loading to the sequencer would solve this problem and increase efficiency in using the flow cell of the sequencer.

Illustrative Embodiments of the Invention

This disclosure includes the following exemplary embodiments of the invention.

Embodiment 1: A method for normalizing a nucleic acid library comprising:
(a) hybridizing single stranded nucleic acid molecules obtained from the library with a hybridization solution, wherein the hybridization solution comprises probes, and wherein the single stranded nucleic acid molecules and the probes form hybridization complexes,
  wherein the single stranded nucleic acid molecules each comprise an A adaptor sequence and a B adaptor sequence, or an A' adaptor sequence and a B' adaptor sequence,
  wherein the A adaptor sequence is a reverse complement of the A' adaptor sequence and the B adaptor sequence is a reverse complement of the B' adaptor sequence,
  wherein each hybridization complex comprises one of the single-stranded nucleic acid molecules and one or more probes,
  wherein the one or more probes each has a sequence that is complementary to the A adaptor sequence, the B adaptor sequence, the A' adaptor sequence, or the B' adaptor sequence, and
  wherein the one or more probes each is conjugated to a first binding member,
(b) contacting the hybridization complexes with solid supports, each solid support conjugated to a second binding member,
  wherein the first binding member binds to the second binding member, thereby causing the solid supports to bind to the hybridization complexes to form solid support-bound hybridization complexes,
(c) collecting the solid support-bound hybridization complexes, and
(d) separating the single stranded nucleic acid molecules from probes in the hybridization complexes, thereby obtaining a normalized library of single stranded nucleic acid molecules.

Embodiment 2: The method of embodiment 1, wherein the single stranded molecules in step (a) are prepared from a double stranded nucleic acid library by the following steps:

(i) ligating A adaptors and B adaptors to a plurality of double stranded double stranded nucleic acid molecules in the double stranded nucleic acid library to form a plurality of adaptor-ligated double stranded nucleic acid molecules, wherein each adaptor-ligated double stranded nucleic acid molecule comprises an A adaptor at one end and a B adaptor at the other end,
wherein each A adaptor is a double stranded adaptor comprising an A adaptor sequence and a A' adaptor sequence, and
wherein each B adaptor is a double stranded adaptor comprising a B adaptor sequence and a B' adaptor sequence,
wherein the A adaptor sequence is a reverse complement of the A' adaptor sequence and the B adaptor sequence is a reverse complement of the B' adaptor sequence, and optionally, amplifying the adaptor-ligated double stranded nucleic acid molecules to form amplified adaptor-ligated double stranded nucleic acid molecules using a DNA polymerase;
(ii) denaturing adaptor-ligated double stranded nucleic acid molecules or amplified adaptor-ligated double stranded nucleic acid molecules to form the single stranded nucleic acid molecules.

Embodiment 3: The method of embodiment 2, wherein the denaturing and the hybridizing steps are performed in the same hybridization solution.

Embodiment 4: The method of embodiment 2 or 3, wherein the amplified adaptor-ligated double stranded nucleic acid molecules are contacted with the hybridization solution to form a reaction mixture, and optionally the reaction mixture still contains the DNA polymerase and/or free nucleotides used for the amplification.

Embodiment 5: The method of any of the preceding embodiments, wherein step (a) comprises mixing the probes with the single stranded nucleic acid molecules to form a hybridization mixture, wherein the amount of the probe as compared to single stranded nucleic acid molecules is selected to normalize libraries, such that the range of relative variation in concentration of normalized libraries as compared to the range of relative variation in concentration of pre-normalized libraries is reduced by at least 30%.

Embodiment 6: The method of any of the preceding embodiments, wherein the A adaptor sequence is a P5 adaptor sequence and the B adaptor is a P7 adaptor sequence, wherein the A' adaptor sequence is a P5' adaptor sequence and the B' adaptor is a P7' adaptor sequence, wherein the P5, P5', P7, and P7'adaptor sequences are configured for analyzing the libraries in next generation sequencing.

Embodiment 7: The method of any of the preceding embodiments, wherein the method further comprises washing the collected solid support-bound hybridization complexes after step (c) and before step (d).

Embodiment 8: The method of any of the preceding embodiments, wherein the nucleic acid molecules in the nucleic acid library are double stranded, wherein the method further comprises denaturing the double stranded nucleic acid molecules to produce the single stranded nucleic acid molecules Embodiment 9: The method of any of the preceding embodiments, wherein the first binding member is biotin and the second binding member is selected from streptavidin, avidin and neutrAvidin.

Embodiment 10: The method of any of the preceding embodiments, wherein the first binding member binds to the second binding member through antibody antigen interaction.

Embodiment 11: The method of any of the preceding embodiments, wherein the single stranded nucleic acid molecules comprise a first single stranded nucleic acid and a second single stranded nucleic acid,
wherein the first single stranded nucleic acid is complementary to the second single stranded nucleic acid,
wherein the first single stranded nucleic acid comprises an A adaptor sequence and a B adaptor sequence, and the second single stranded nucleic acid comprises an A' adaptor sequence and B' adaptor sequence.

Embodiment 12: The method of any of the preceding embodiments, wherein the step (a) comprises:
hybridizing one or more first probes to the first strand to form a first hybridization complex, wherein the one or more first probes are complementary to the A adaptor sequence or the B adaptor sequence, and/or
hybridizing one or more second probes to the second strand to form a second hybridization complex, wherein the one or more second probes are complementary to the A' adaptor sequence or the B' adaptor sequence.

Embodiment 13: The method of embodiment 12, wherein each of the one or more first probes shares no more than 10 consecutive complementary nucleotides with each of the one or more second probes.

Embodiment 14: The method of embodiment 12, wherein each of the one or more first probes shares no more than 7 consecutive complementary nucleotides with each of the one or more second probes.

Embodiment 15: The method of embodiment 12, wherein each of the one or more first probes shares no complementary nucleotide with the one or more second probes.

Embodiment 16: The method of embodiment 1, wherein the one or more probes each has a length of 18 to 35 nucleotides.

Embodiment 17: The method of any of the preceding embodiments, wherein the one or more probes has a sequence of SEQ ID NO: 3 or SEQ ID NO: 4.

Embodiment 18: The method of any of the preceding embodiments, wherein the solid supports are beads.

Embodiment 19: The method of any of the preceding embodiments, wherein the beads are paramagnetic beads and the collecting the complexes is by placing the complexes in a magnetic field.

Embodiment 20: The method of any of the preceding embodiments, wherein the one or more probes each further comprise a spacer between the first binding member and its nucleic acid sequence, wherein the spacer comprises a simple carbon or ethylene glycol chain, or multiples of either.

Embodiment 21: The method of any of the preceding embodiments, wherein hybridizing single stranded nucleic acid molecules with probes is by mixing the probes with the single stranded nucleic acid molecules to form a hybridization mixture, wherein the ratio of the molar amount of the probes to the molar amount of single stranded nucleic acids ranges from 0.025:1 to 16.7:1.

Embodiment 22: The method of embodiment 2 or 8, wherein the concentration of the double stranded nucleic acid library ranges from 15 nM to 200 nM.

Embodiment 23: The method of any of the preceding embodiments, wherein the total concentration of the probes ranges from 10 nM to 500 nM.

Embodiment 24: The method of any of the preceding embodiments, wherein the amount of the solid supports ranges from 50 to 600 µg per reaction.

Embodiment 25: The method of embodiment 2 or 8, wherein the denaturing is under the temperature that ranges from 102° C.-110° C.

Embodiment 26: The method of any of the preceding embodiments, wherein the single stranded nucleic acid molecules are hybridized to probes for a period of time that ranges from 8 to 16 minutes.

Embodiment 27: The method of any of the preceding embodiments, wherein step (b) comprising incubating the hybridization complexes with the solid supports for a period of time that ranges from 20 to 40 minutes.

Embodiment 28: The method of any of the preceding embodiments, wherein the A adaptor sequence, the A' adaptor sequence, the B adaptor sequence, or the B' adaptor sequence are configured to be able to bind to an oligo immobilized on a flow cell of a sequencer.

Embodiment 29: The method of any of the preceding embodiments, wherein one or more of the A adaptor sequence, the A' adaptor sequence, the B adaptor sequence, or the B' adaptor sequence comprises a sample index sequence.

Embodiment 30: The method of any of the preceding embodiments, wherein the A adaptor sequence comprises SEQ ID NO: 10 and the B adaptor sequence comprise SEQ ID NO: 13.

Embodiment 31: The method of any of the preceding embodiments, wherein the A' adaptor sequence comprises SEQ ID NO: 11, and the B' adaptor sequence comprises SEQ ID NO: 12.

Embodiment 32: The method of any of the preceding embodiments, wherein the method further comprises sequencing the normalized library of single stranded nucleic acid molecules.

Embodiment 33: A hybridization solution comprising one or more probes and a salt, wherein one or more probes each have a sequence that is complementary to the A adaptor sequence, the B adaptor sequence, the A' adaptor sequence, or the B' adaptor sequence, wherein the one or more probes, each conjugated to a first binding member.

Embodiment 34: The hybridization solution of embodiment 33, wherein the salt is present in a concentration ranging from 75 mM to 1200 mM.

Embodiment 35: The hybridization solution of embodiment 33 or 34, wherein the first binding member is biotin.

Embodiment 36: The hybridization solution of any one of embodiments 33-35, wherein the one or more probes have the same sequence.

Embodiment 37: The hybridization solution of any one of embodiments 33-36, wherein the one or more probes comprises a first probe and a second probe, wherein the first probe being complementary to the A adaptor sequence or the B adaptor sequence, and the second probe being complementary to the A' adaptor sequence or the B' adaptor sequence.

Embodiment 38: A reaction mixture comprising a hybridization solution of any of embodiments 33-37 and single stranded nucleic acid molecules.

Embodiment 39: The reaction mixture of embodiment 38, wherein the reaction mixture further comprises a solid support.

Embodiment 40: The reaction mixture of embodiment 38, wherein the solid support is a paramagnetic bead.

Embodiment 41: A kit comprising (i) probes each have a sequence that is complementary to the A adaptor sequence, the B adaptor sequence, the A' adaptor sequence, or the B' adaptor sequence, and
(ii) a paramagnetic solid support,
wherein the solid support is conjugated to a second binding member, and
wherein the first binding member is capable of binding to the second binding member.

Embodiment 42: The kit of embodiment 41, wherein the probes comprise one or more first probes have a sequence that is complementary to the A adaptor sequence or the B adaptor sequence, and one or more second probes have a sequence that is complementary to the A' adaptor sequence and the B' adaptor sequence.

Embodiment 43: The kit of embodiment 41, wherein the one or more first probes have a sequence of SEQ ID NO: 3 and the one or more second probes have a sequence of SEQ ID NO: 4.

Embodiment 44: A method of normalizing a plurality of nucleic acid libraries which are of different concentrations in a pre-normalized range, wherein the method comprises:
normalizing each library according to embodiment 1 to obtain a normalized library, whereby producing a plurality of normalized libraries of different concentrations in a normalized range,
wherein the normalized range is narrower than the pre-normalized range.

Embodiment 45: The method of embodiment 44, wherein the relative variation in concentration among the normalized libraries is not greater than 8 fold.

Embodiment 46: The method of embodiment 44 or 45, further comprising sequencing the single-stranded nucleic acid molecules from each normalized library, and determining total aligned sequencing counts, wherein the standard deviation for the total aligned sequencing counts is within 25% of the mean aligned sequencing counts.

Embodiment 47: The method of any of embodiments 44-46, wherein normalizing each library according to embodiment 1 comprises hybridizing single stranded nucleic acid molecules with probes is by mixing the probes with the single stranded nucleic acid molecules to form a hybridization mixture, wherein the ratio of the molar amount of the probes to the molar amount of single stranded nucleic acids in the hybridization mixture ranges from 0.025:1 to 16.7:1.

Embodiment 48: A method of normalizing a nucleic acid library, wherein the nucleic acid library comprises a plurality of double stranded nucleic acid molecules, the method comprising:
(a) ligating A adaptors and B adaptors to the plurality of double stranded double stranded nucleic acid molecules in the library to form a plurality of adaptor-ligated double stranded nucleic acid molecules, wherein each adaptor-ligated double stranded nucleic acid molecule comprises an A adaptor at one end and a B adaptor at the other end,
wherein each A adaptor is a double stranded adaptor comprising an A adaptor sequence and a A' adaptor sequence, and
wherein each B adaptor is a double stranded adaptor comprising a B adaptor sequence and a B' adaptor sequence,
wherein the A adaptor sequence is a reverse complement of the A' adaptor sequence and the B adaptor sequence is a reverse complement of the B' adaptor sequence,;
(b) denaturing the plurality of adaptor-ligated double stranded nucleic acid molecules to form single stranded nucleic acid molecules, wherein each single stranded nucleic acid molecules comprises an A adaptor sequence and a B adaptor sequence, or an A' adaptor sequence and a B' adaptor sequence;

(c) contacting the single stranded nucleic acid molecules with a hybridization buffer, wherein the hybridization buffer comprises a plurality of probes.

(d) hybridizing the single stranded nucleic acid molecules with probes to form hybridization complexes, wherein each hybridization complex comprises one of the single-stranded nucleic acid molecules and one or more probes, wherein the one or more probes each has a sequence that is complementary to the A adaptor sequence, the B adaptor sequence, the A' adaptor sequence, or the B' adaptor sequence, and wherein the one or more probes each is conjugated to a first binding member, (e) contacting the hybridization complexes with solid supports, each solid support conjugated to a second binding member, wherein the first binding member binds to the second binding member, thereby causing the solid supports to bind to the hybridization complexes to form solid support-bound hybridization complexes, (f) collecting the solid support-bound hybridization complexes, and (g) separating the single stranded nucleic acid molecules from probes in the hybridization complexes, thereby obtaining a normalized library of single stranded nucleic acid molecules.

EXAMPLES

The following examples are provided to illustrate but not to limit the invention.

Example I. Normalization Reduces Coefficient of Variation of the Total Aligned Sequencing Counts of the Libraries This example shows the effect of normalizing libraries on sequencing. Samples from 95 individual patient libraries were normalized using the standard method (as shown in FIG. 1A). Samples from the same 95 individual patient libraries were not normalized and used as non-normalized controls. The normalized libraries and non-normalized libraries were pooled separately and sequenced in parallel. The sequence reads were aligned to human reference genome hg38 and the total aligned sequencing count for each library (normalized and non-normalized) was determined. The coefficient of variation (CV) was calculated by dividing the standard deviation of the total aligned sequencing counts across all 95 libraries by the mean of the total aligned sequencing counts. The value was then multiplied by 100 and reported as a percentage.

Figures 4A, 4B:
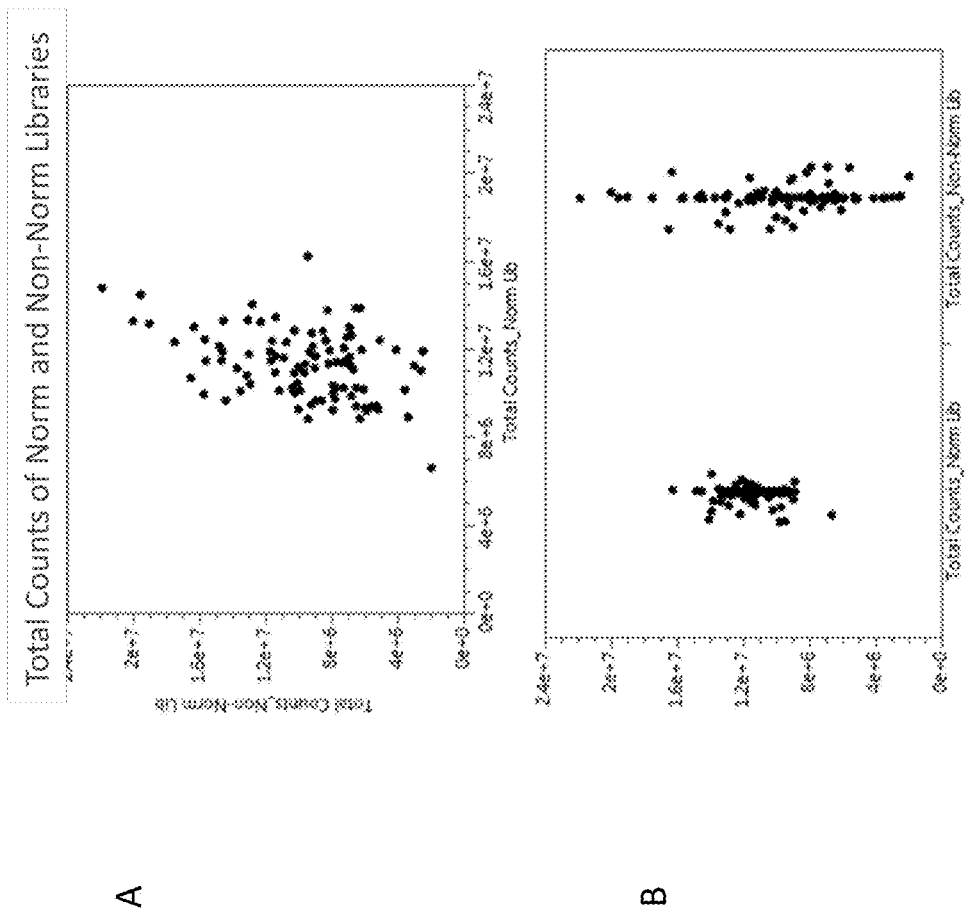
FIGS. 4A and 4B show the effects of normalized versus non-normalized libraries on sequencing results. The data represent total aligned sequencing counts for 95 individual patient libraries. In one set of samples, the libraries were not normalized. In another set of samples, the libraries were normalized using the standard method as illustrated in FIG. 1.

The results show that the CV of the total aligned sequencing counts of the normalized libraries was 15%, a significant reduction as compared to the CV of the total aligned sequencing counts of the non-normalized libraries, which was 43%. See FIGS. 4A and 4B. A low CV (e.g., less than 25%,) indicates that sequence reads from individual libraries are close to be equally represented in the results, and that the sequencing is efficient.

Example II. Normalizing Nucleic Acid Libraries Using CapNorm

This example describes using capNorm to normalize nucleic acid libraries. Three hundred and thirty-seven (337) samples were obtained, one sample per patient. The ends of the double stranded nucleic acid molecules in the samples were repaired, and then ligated with a P5 adaptor and a P7 adaptor on both ends to prepare libraries, one library per patient. The concentrations of these libraries were measured and they ranged from 14 to 137 nM. The P5 adaptor comprises a P5 adaptor sequence having the sequence of SEQ ID NO: 1 and a P5' adaptor sequence having the sequence of SEQ ID NO: 16, the P5 adaptor sequence is complementary to the P5' adaptor sequence. The P7 adaptor comprises a P7 adaptor sequence having the sequence of SEQ ID NO: 2 (comprising SEQ ID NOS: 14 and 15) and a P7' adaptor sequence having the sequence of SEQ ID NOS: 12 and 17, and the P7 adaptor sequence is complementary to the P7' adaptor sequence. The double stranded nucleic acid molecules in the libraries were amplified by PCR using primers having complementary sequences to portions of the P5 adaptor and the P7 adaptor.

Twenty (20) µl of hybridization solution, comprising a mixture of 10 mM Tris-HCl (pH 8.5), 375 nM NaCl, 0.05% Tween-20, and 12.5 nM biotinylated probes BioTinTEG-ILMN_P5f (comprising a sequence of SEQ ID NO: 3) and 12.5 nM BioTinTEG-ILMN_P5rc (comprising a sequence of SEQ ID NO: 4), as shown in FIG. 9, was combined with 40 µl of the double stranded nucleic acid molecules from each library. The libraries were amplified before being contacted with the probes. The mixture was at heated to denature the double stranded nucleic acid molecules and then allowed to cool at room temperature, during which the double stranded molecules were denatured and the probes hybridized to the single stranded nucleic acid molecules to form hybridization complexes.

The solid support used in this experiment was a MyOne stepavidin C1 bead plate (Thermo Fisher Scientific, Waltham, Mass.). The bead plate contained 10 µl beads per well, @ 10 mg/ml. Before use, the beads were washed by adding a wash buffer and remove the supernatant from the beads while the bead plate was on a magnet plate. After the wash, the beads were then resuspended in 40 µl wash buffer and ready to be used.

To capture the libraries, 60 µl mixture containing the hybridization complexes was added to the beads in each well, and the beads were resuspended and incubated with the hybridization complexes at room temperature to allow the beads to bind to the complexes. After the incubation, the plate was placed on a magnet plate to pellet beads, which were bound with the hybridization complexes. Supernatants in the wells were removed and discarded to remove the unbound materials. One hundred and fifty (150) µl universal wash buffer was then added to the bead-bound hybridization complexes while still on magnet. The supernatants were removed and discarded, and this wash step was repeated at least twice.

To elute the single stranded nucleic acid molecules from the beads, the plate was removed from the magnet plate. Sixty (60) µl elution buffer (comprising a mixture of 10 mM Tris-HCl, pH 8.5 and 0.01% Tween 20) was added to the beads, which were bound by hybridization complexes, and mixed to resuspend the beads. The beads were incubated in the elution buffer at 85° C. for 2 minutes to denature and release the single stranded nucleic acid molecules from the probes, which were still bound to the beads. The plate was then placed on the magnet plate to pellet the beads. The eluates from the beads, which contained normalized libraries, were collected and measured for the nucleic acid concentration in each library.

Figures 5A, 5B:
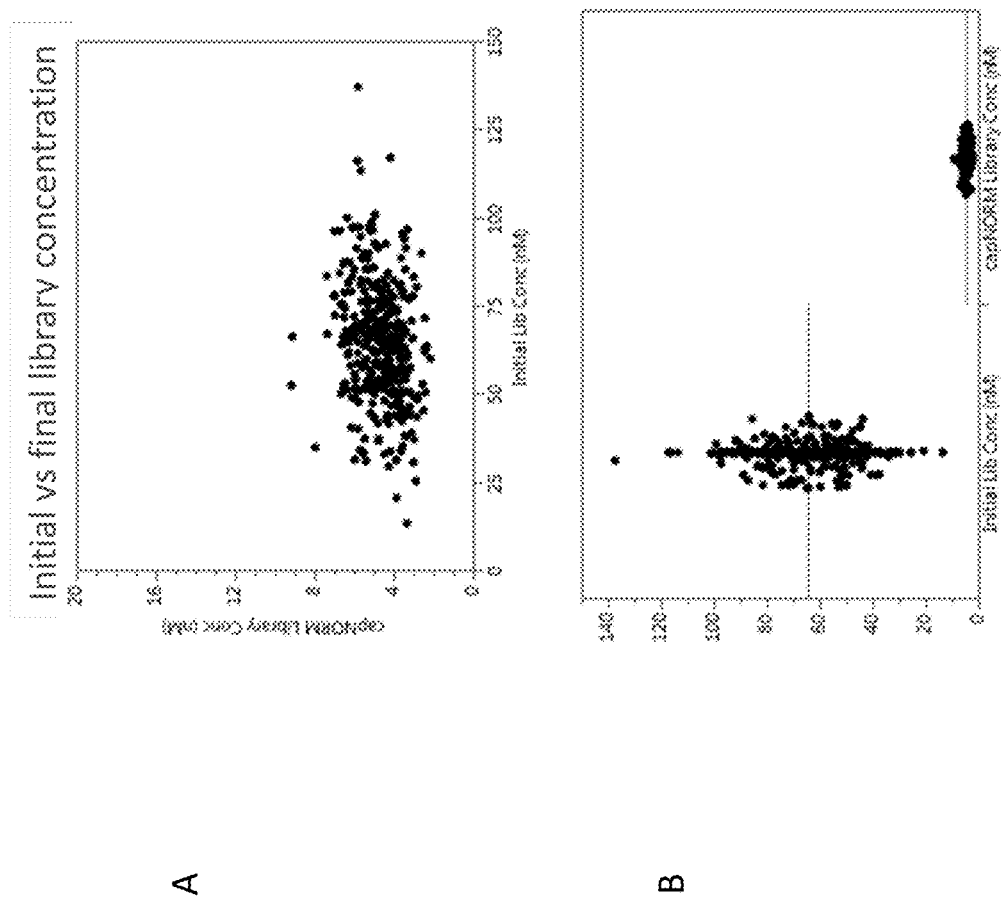
FIGS. 5A and 5B show the results from normalizing 377 patient libraries using capNorm. These 377 individual patient libraries had initial concentrations ranging from 14 to 137 nM. After normalization, the normalized libraries have concentrations ranging from 2-9 nM. The Y axis in both
Figure 6:
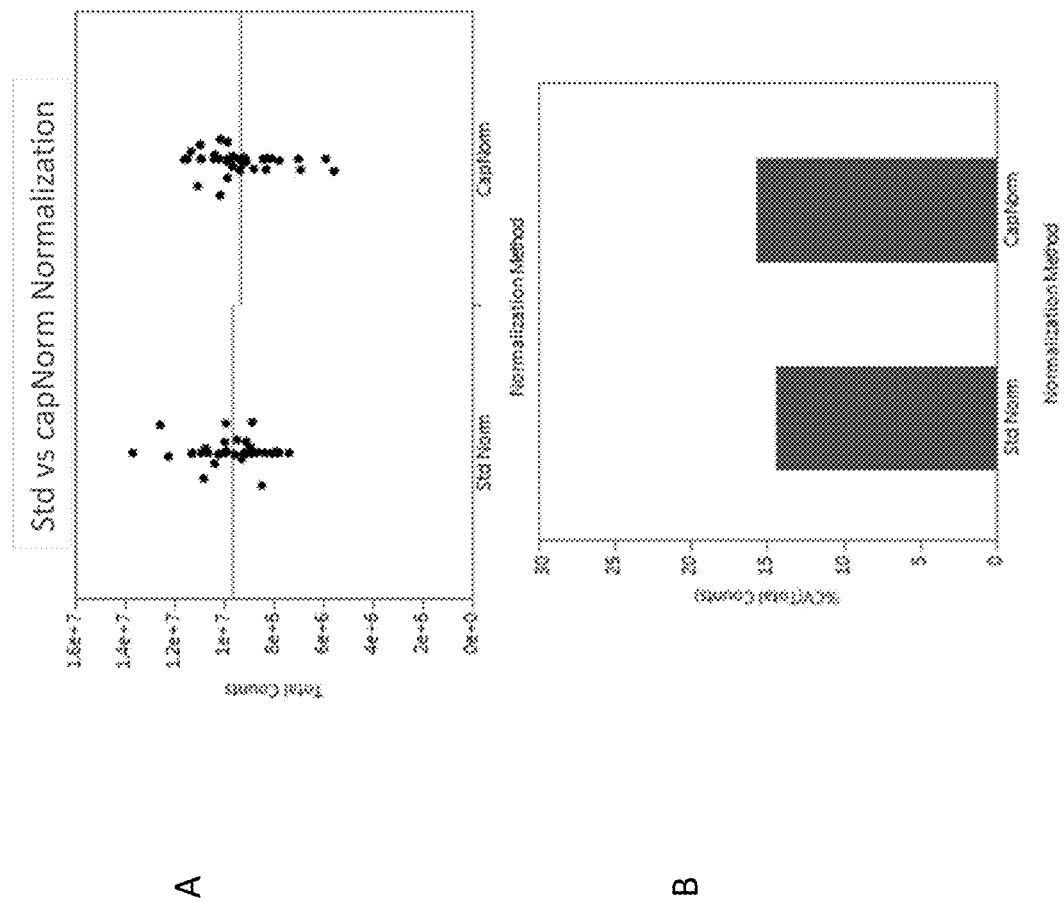
FIG. 6A and FIG. 6B compare the sequencing results of 36 libraries that were normalized using standard method versus using capNorm. The result showed that the CV of the total aligned sequencing counts of libraries normalized using capNorm was comparable to that of the total aligned sequencing counts of libraries normalized using the stand method as shown in FIG. 1A.

As shown in FIG. 5A and FIG. 5B, the 377 patient libraries, after normalization using capNorm, show concentrations that was within a range of 2-9 nM, or a range of 4.5 fold (calculated based on the ratio between the highest concentration, 9 nM, and the lowest concentration of the range, 2 nM). The concentration range from the normalized libraries was much narrower than the initial concentration range of 9.8 fold (from 14 to 137 nM). The CV of the concentrations of the normalized libraries was less than 25%, meeting the requirement for most of the downstream biochemical analyses.

Example III. CapNorm Versus Standard Normalization Method

The capNorm method, which can be completed in a shorter period than the standard method, can achieve similar results as the standard method. In this study, 36 libraries were normalized by the standard method, as well as by capNorm. The normalized libraries were sequenced and the total aligned sequencing counts were determined. As shown in FIG. 6, both the mean total aligned sequencing counts and the CV of the total aligned sequencing counts were comparable between the two methods. The CV of the total aligned sequencing counts for the libraries normalized using the standard method was 14.5% and the CV using capNorm was 15.7%, both well below the target CV value of 25%.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

Informal sequence listing:

| SEQ ID | Description | Sequences |
|---|---|---|
| 1 | P5 adaptor sequence | 5'-AATGATACGGCGACCACCGAGATCTACACTCTTTCCCTACACGACGCTCTTCCGATCT-3' |
| 2 | P7 adaptor sequence | 5'-AGATCGGAAGAGCACACGTCTGAACTCCAGTCAC[i7]ATCTCGTATGCCGTCTTCTGCTTG-3' |
| 14 | The first subsequence of the P7 adaptor sequence | 5'-AGATCGGAAGAGCACACGTCTGAACTCCAGTCAC-3' |
| 15 | The second subsequence of the P7 adaptor sequence | 5'-ATCTCGTATGCCGTCTTCTGCTTG-3' |
| 3 | P5f | 5'-CCT ACA CGA CGC TCT TCC GAT CT-3' |
| 4 | P5rc | 5'-GTG TAG GGA AAG AGT GTA GAT CTC GGT-3' |
| 5 | P5rc2 | 5'-GTG TAG ATC TCG GTG GTC GCC-3' |
| 6 | P7rc1 | 5'-TGA CTG GAG TTC AGA CGT GTG CTC-3' |
| 7 | P7rc2 | 5'-CAA GCA GAA GAC GGC ATA CGA GAT-3' |
| 8 | P7rc3 | 5'-GTT CAG ACG TGT GCT CTT CCG ATC-3' |
| 9 | P7rc4 | 5'-CTG GAG TTC AGA CGT GTG CTC TTC-3' |
| 10 | P5 sequence | 5'-AATGATACGGCGACCACCGAGA-3' |
| 11 | P5' sequence | 5'-TCTCGGTGGTCGCCGTATCATT-3' |
| 12 | P7' sequence | 5'-CAAGCAGAAGACGGCATACGAGAT-3' |
| 13 | P7 sequence | 5'-ATCTCGTATGCCGTCTTCTGCTTG-3' |
| 14 | Part 1 of the P7 adaptor sequence | 5'-AGATCGGAAGAGCACACGTCTGAACTCCAGTCAC-3' |
| 15 | Part 2 of the P7 adaptor sequence | 5'-ATCTCGTATGCCGTCTTCTGCTTG-3' |
| 16 | P5' adaptor sequence | 5'-AGATCGGAAGAGCGTCGTGTAGGGAAAGAGTGTAGATCTCGGTGGTCGCCGTATCATT-3' |
|  | P7' adaptor sequence | 5'-CAAGCAGAAGACGGCATACGAGAT[i7]GTGACTGGAGTTCAGACGTGTGCTCTTCCGATCT-3' |

Informal sequence listing:

| SEQ ID | Description | Sequences |
|---|---|---|
| 12 | The first subsequence of the P7' adaptor sequence | 5'-CAAGCAGAAGACGGCATACGAGAT-3' |
| 17 | The second subsequence of the P7' adaptor sequence | 5'-GTGACTGGAGTTCAGACGTGTGCTCTTCCGATCT-3' |

We claim:

1. A method for normalizing a nucleic acid library comprising:
    (a) contacting at least some of single-stranded nucleic acid molecules Obtained from the library with a solution comprising a salt and one or more probes,
        wherein each of at least some of the single-stranded nucleic acid molecules comprises an A adaptor sequence and a B adaptor sequence,
        wherein the one or more probes each has a sequence that is complementary to the A adaptor sequence or the B adaptor sequence,
        wherein the one or more probes hybridize to the single-stranded nucleic acid molecules to form hybridization complexes, and
        wherein the one or more probes each is conjugated to a first binding member,
    (b) contacting the hybridization complexes with solid supports, each solid support conjugated to a second binding member,
        wherein the first binding member binds to the second binding member, thereby causing the solid supports to bind to the hybridization complexes to form solid support-bound hybridization complexes,
    (c) collecting the solid support-bound hybridization complexes, and
    (d) separating the single-stranded nucleic acid molecules from probes in the hybridization complexes, thereby obtaining a normalized library of single-stranded nucleic acid molecules.

2. The method of claim 1, wherein the A adaptor sequence is a P5 adaptor sequence and the B adaptor sequence is a P7 adaptor sequence, wherein the P5 and P7 adaptor sequences are configured for analyzing the library in next generation sequencing.

3. The method of claim 1, wherein the method further comprises washing the collected solid support-bound hybridization complexes after step (c) and before step (d).

4. The method of claim 1, wherein the nucleic acid molecules in the nucleic acid library are double-stranded, wherein the method further comprises denaturing the double stranded nucleic acid molecules to produce the single-stranded nucleic acid molecules.

5. The method of claim 1, wherein the first binding member is biotin and the second binding member is selected from streptavidin, avidin and neutrAvidin.

6. The method of claim 1, wherein the first binding member binds to the second binding member through antibody antigen interaction.

7. The method of claim 1, wherein the single-stranded nucleic acid molecules comprise a first single-stranded nucleic acid and a second single-stranded nucleic acid,
wherein the first single stranded nucleic acid is complementary to the second single-stranded nucleic acid,
wherein the first single-stranded nucleic acid comprises an A adaptor sequence and a B adaptor sequence, and the second single-stranded nucleic acid comprises an A' adaptor sequence and a B' adaptor sequence,
wherein the A adaptor sequence is a reverse complement of the A' adaptor sequence and the B adaptor sequence is a reverse complement of the B' adaptor sequence.

8. The method of claim 7, wherein step (a) comprises:
hybridizing one or more first probes to the first single stranded nucleic acid to form a first hybridization complex, wherein the one or more first probes are complementary to the A adaptor sequence or the B adaptor sequence, and/or
hybridizing one or more second probes to the second single stranded nucleic acid to form a second hybridization complex, wherein the one or more second probes are complementary to the A' adaptor sequence or the B' adaptor sequence.

9. The method of claim 8, wherein each of the one or more first probes shares no more than 10 consecutive complementary nucleotides with each of the one or more second probes.

10. The method of claim 9, wherein each of the one or more first probes shares no complementary nucleotide with the one or more second probes.

11. The method of claim 1, wherein the one or more probes each has a length of 18 to 35 nucleotides.

12. The method of claim 1, wherein the one or more probes has a sequence of SEQ ID NO: 3, or SEQ ID NO: 4, SEQ ID NO: 5, SEQ ID NO: 6, SEQ ID NO: 7, SEQ ID NO: 8, and/or SEQ ID NO: 9.

13. The method of claim 1, wherein the solid supports are beads.

14. The method of claim 1, wherein the solid supports are paramagnetic beads and the collecting the complexes is by placing the complexes in a magnetic field.

15. The method of claim 1, wherein the one or more probes each further comprise a spacer between the first binding member and its nucleic acid sequence, wherein the spacer comprises a simple carbon or ethylene glycol chain, or multiples of either.

16. The method of claim 1, wherein hybridizing single stranded nucleic acid molecules with probes is by mixing the probes with the single stranded nucleic acid molecules to form a hybridization mixture, wherein the ratio of the molar amount of the probes to the molar amount of single stranded nucleic acids ranges from 0.025:1 to 16.7:1.

17. The method of claim 1, wherein the A adaptor sequence and the B adaptor sequence are configured to be able to bind to an oligo immobilized on a flow cell of a sequencer.

18. The method of claim 1, wherein one or more of the A adaptor sequence and the B adaptor sequence comprises a sample index sequence.

19. The method of claim 1, wherein the A adaptor sequence comprises SEQ ID NO: 10 and the B adaptor sequence comprises SEQ ID NO: 13.

20. The method of claim 7, wherein the A' adaptor sequence comprises SEQ ID NO: 11, and the B' adaptor sequence comprises SEQ ID NO: 12.

21. The method of claim 1, wherein the method further comprises sequencing the normalized library of single-stranded nucleic acid molecules.

22. The method of claim 1, wherein the nucleic acid library is a double-stranded nucleic acid library, and wherein the method comprises denaturing the double-stranded nucleic acid library to form the single-stranded nucleic acid molecules in step (a).

23. A method of normalizing a plurality of nucleic acid libraries that are of different concentrations in a pre-normalized range, wherein each nucleic acid library comprises a plurality of double-stranded nucleic acid molecules,
wherein the method comprises: for each nucleic acid library,
(a) ligating double-stranded adaptors A and B to two ends of each of the plurality of double-stranded nucleic acid molecules,
(b) denaturing the plurality of double-stranded nucleic acid molecules to produce a mixture of single-stranded nucleic acid molecules,
wherein each of at least some of the single-stranded nucleic acid molecules comprises an A adaptor sequence and a B adaptor sequence,
(c) adding a solution comprising salt and one or more probes to the mixture,
wherein a similar amount of probes is added to each mixture of single-stranded nucleic acid molecules,
wherein the one or more probes each has a sequence that is complementary to the A adaptor sequence or the B adaptor sequence,
wherein the one or more probes hybridize to the single-stranded nucleic acid molecules to form hybridization complexes, and
wherein the one or more probes each is conjugated to a first binding member,
(d) contacting the hybridization complexes with solid supports, each solid support conjugated to a second binding member,
wherein the first binding member binds to the second binding member, thereby causing the solid supports binding to the hybridization complexes to form solid support-bound hybridization complexes,
(e) collecting the solid support-bound hybridization complexes, and
(f) separating the single-stranded nucleic acid molecules from probes in the hybridization complexes by adding elution buffer to the solid support-bound hybridization complexes, thereby obtaining a normalized library of single-stranded nucleic acid molecules, thereby producing a plurality of normalized libraries of different concentrations in a normalized range, wherein the normalized range is narrower than the pre-normalized range.

24. The method of claim 23, wherein the relative variation in concentration among the normalized libraries is not greater than 8-fold.

25. The method of claim 23, further comprising sequencing the single-stranded nucleic acid molecules from each normalized library, and determining total aligned sequencing counts, wherein the standard deviation for the total aligned sequencing counts is within 25% of the mean aligned sequencing counts.

26. The method of claim 23, wherein normalizing each library comprises hybridizing single-stranded nucleic acid molecules with probes by mixing the probes with the single-stranded nucleic acid molecules to form a hybridization mixture, wherein the ratio of the molar amount of the probes to the molar amount of single stranded nucleic acids in the hybridization mixture ranges from 0.025:1 to 16.7:1.

27. A kit for normalizing a nucleic acid library, wherein the nucleic acid library comprises double-stranded nucleic acid molecules that is ligated to double-stranded adaptors A and B at two ends, wherein double-stranded adaptor A comprises an A adaptor sequence and an A' adaptor sequence, wherein double stranded adaptor B comprises a B adaptor sequence and a B' adaptor sequence, the kit comprising
(i) a solution comprising a salt and one or more probes, wherein
  each of the one or more probes comprises a sequence that is complementary to a portion of the A adaptor sequence, a portion of the B adaptor sequence, or a portion of the B' adaptor sequence; wherein the A adaptor sequence is a P5 adaptor sequence and the B adaptor sequence is a P7 adaptor sequence;
  wherein each of the one or more prohes is conjugated to a first binding member; and
(ii) a paramagnetic solid support,
  wherein the solid support is conjugated to a second binding member, and
  wherein the first binding member is capable of binding to the second binding member.

28. The kit of claim 27, wherein the one or more probes comprise one or more first probes having a sequence that is complementary to the A adaptor sequence or the B adaptor sequence, and one or more second probes having a sequence that is complementary to the A' adaptor sequence or the B' adaptor sequence.

29. The kit of claim 28, wherein the one or more first probes have a sequence of SEQ ID NO: 3, SEQ ID NO: 4, SEQ ID NO: 5, SEQ ID NO: 6, SEQ ID NO: 7, SEQ ID NO: 8, and/or SEQ ID NO: 9, and the one or more second probes have a sequence of SEQ ID NO: 3, SEQ ID NO: 4, SEQ ID NO: 5, SEQ ID NO: 6, SEQ ID NO: 7, SEQ ID NO: 8, and/or SEQ ID NO: 9.

* * * * *

SEQUENCE LISTING

<160> NUMBER OF SEQ ID NOS: 21

<210> SEQ ID NO 1
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
aatgatacgg cgaccaccga gatctacact ctttccctac acgacgctct tccgatct        58

<210> SEQ ID NO 2

<400> SEQUENCE: 2

000

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic probe

<400> SEQUENCE: 3
cctacacgac gctcttccga tct        23

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic probe

<400> SEQUENCE: 4
gtgtagggaa agagtgtaga tctcggt        27

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic probe

<400> SEQUENCE: 5
gtgtagatct cggtggtcgc c        21

```
<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tgactggagt tcagacgtgt gctc                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
caagcagaag acggcatacg agat                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
gttcagacgt gtgctcttcc gatc                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ctggagttca gacgtgtgct cttc                                              24

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
aatgatacgg cgaccaccga ga                                                22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tctcggtggt cgccgtatca tt                                                22
```

```
<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
caagcagaag acggcatacg agat                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atctcgtatg ccgtcttctg cttg                                          24

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agatcggaag agcacacgtc tgaactccag tcac                               34

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
atctcgtatg ccgtcttctg cttg                                          24

<210> SEQ ID NO 16
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
agatcggaag agcgtcgtgt agggaaagag tgtagatctc ggtggtcgcc gtatcatt     58

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgactggag ttcagacgtg tgctcttccg atct                               34

<210> SEQ ID NO 18
```

-continued

```
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aatgatacgg cgaccaccga gatctacac                                          29

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acactctttc cctacacgac gctcttccga tct                                     33

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
agatcggaag agcgtcgtgt agggaaagag tgt                                     33

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtgtagatct cggtggtcgc cgtatcatt                                          29
```